(12) United States Patent
Ago et al.

(10) Patent No.: US 11,737,837 B2
(45) Date of Patent: Aug. 29, 2023

(54) SURGICAL INSTRUMENT

(71) Applicant: MEDICAROID CORPORATION, Kobe (JP)

(72) Inventors: Kenji Ago, Kobe (JP); Jota Ida, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 272 days.

(21) Appl. No.: 17/213,098

(22) Filed: Mar. 25, 2021

(65) Prior Publication Data

US 2021/0298849 A1 Sep. 30, 2021

(30) Foreign Application Priority Data

Mar. 27, 2020 (JP) ................................. 2020-057206

(51) Int. Cl.
| | | |
|---|---|---|
| *A61B 34/30* | (2016.01) | |
| *A61B 17/128* | (2006.01) | |
| *A61B 17/32* | (2006.01) | |
| *A61B 17/3201* | (2006.01) | |
| *A61B 34/00* | (2016.01) | |
| *A61B 17/00* | (2006.01) | |
| *A61B 34/37* | (2016.01) | |

(52) U.S. Cl.
CPC .......... *A61B 34/30* (2016.02); *A61B 17/1285* (2013.01); *A61B 17/3201* (2013.01); *A61B 17/320016* (2013.01); *A61B 34/71* (2016.02); *A61B 34/37* (2016.02); *A61B 2017/00225* (2013.01); *A61B 2017/00477* (2013.01); *A61B 2034/302* (2016.02)

(58) Field of Classification Search
CPC ......... A61B 34/30; A61B 34/37; A61B 34/71; A61B 17/1285; A61B 17/320016; A61B 17/3201; A61B 17/29; A61B 17/06061; A61B 2017/00225; A61B 2017/00477; A61B 2017/00353; A61B 2034/302
USPC .................................................. 606/142, 139
See application file for complete search history.

(56) References Cited

U.S. PATENT DOCUMENTS

| | | | | |
|---|---|---|---|---|
| 5,456,695 | A | * | 10/1995 | Herve Dallemagne ...................... A61B 17/29 606/198 |
| 6,394,998 | B1 | * | 5/2002 | Wallace ................. A61B 34/35 901/29 |
| 7,125,403 | B2 | | 10/2006 | Julian et al. |
| 2007/0142851 | A1 | * | 6/2007 | Sixto ....................... A61B 17/08 606/153 |
| 2008/0255589 | A1 | * | 10/2008 | Blakeney ............ A61B 17/1285 606/142 |

(Continued)

*Primary Examiner* — Tan-Uyen T Ho
*Assistant Examiner* — Regina Vahey
(74) *Attorney, Agent, or Firm* — Metrolex IP Law Group, PLLC

(57) ABSTRACT

A surgical instrument according to an embodiment may include: a housing that is to be attached to a driving unit of a robot arm and is provided with a plurality of driven members to be driven by a plurality of drive members of the driving unit; a shaft whose one end portion is connected to the housing; a plurality of end effectors; a support body that is rotatably supported by the other end portion of the shaft and rotatably supports the plurality of end effectors; and a plurality of driving elements that are respectively connected to the plurality of driven members to drive the plurality of end effectors and the support body to rotate.

19 Claims, 9 Drawing Sheets

(56) References Cited

U.S. PATENT DOCUMENTS

| | | | |
|---|---|---|---|
| 2012/0209305 A1* | 8/2012 | Deodhar | A61B 17/295 606/170 |
| 2012/0239080 A1* | 9/2012 | Fan | A61B 17/0469 606/205 |
| 2014/0276970 A1* | 9/2014 | Messerly | A61B 17/320092 606/142 |
| 2015/0150635 A1* | 6/2015 | Kilroy | B25J 17/02 606/130 |
| 2016/0213377 A1* | 7/2016 | Shankarsetty | A61B 17/1285 |
| 2020/0022765 A1* | 1/2020 | Limon | A61B 17/0218 |

* cited by examiner

SURGICAL INSTRUMENT

CROSS REFERENCE TO RELATED APPLICATIONS

This application claims priority to Japanese Patent Application No. 2020-057206 filed on Mar. 27, 2020, the entire contents of which are incorporated herein by reference.

BACKGROUND

The disclosure may relate to a surgical instrument and may especially relate to a surgical instrument including one or more end effectors.

In a related art, it may be desired to shorten a surgery time in order to improve an operating rate of an operating room and reduce a burden on a patient.

For example, U.S. Pat. No. 7,125,403 discloses that a surgical instrument including an end effector that can hold one clip and a cartridge or a tool that can load multiple clips are both inserted into a surgery site inside a body, and then a clip is attached to the end effector of the surgical instrument at the surgical site inside the body. With this, the work of pulling out the surgical instrument from the surgical site in order to attach a next clip to the end effector can be omitted, and the surgical time can be shortened.

SUMMARY

However, in such a surgical instrument disclosed in U.S. Pat. No. 7,125,403, since the end effector can hold only one clip at a time, it may be necessary to attach a next clip to the end effector each time such a next clip is to be used. Further, in a case of performing cutting a blood vessel after clipping, it may be necessary to remove the surgical instrument with an end effector dedicated for clipping operation from the surgical site and insert the surgical instrument with another end effector dedicated for cutting operation such as scissors into the surgical site. Therefore, there may be room for further shortening the surgery time.

An object of an embodiment of the disclosure may be to provide a surgical instrument that is capable of shortening a surgery time.

A surgical instrument according to a first aspect of the disclosure may include: a housing that is to be attached to a driving unit of a robot arm and is provided with a plurality of driven members to be driven by a plurality of drive members of the driving unit; a shaft whose one end portion is connected to the housing; a plurality of end effectors; a support body that is rotatably supported by the other end portion of the shaft and rotatably supports the plurality of end effectors; and a plurality of driving elements that are respectively connected to the plurality of driven members to drive the plurality of end effectors and the support body to rotate.

As described above, the surgical instrument according to the first aspect may include: the plurality of end effectors; the support body that is rotatably supported by the other end portion of the shaft and rotatably supports the plurality of end effectors; and the plurality of driving elements that are respectively connected to the plurality of driven members to drive the plurality of end effectors and the support body to rotate. With this configuration, since the single surgical instrument is equipped with the plurality of end effectors, it is possible to reduce the number of times the surgical instrument (end effector) is inserted into and removed from a surgical site, and reduce the number of times accessories such as clips are attached to the surgical instrument. As a result, the surgery time can be shortened.

A surgical instrument according to a second aspect of the disclosure may include: a housing that is to be attached to a driving unit of a robot arm and is provided with a plurality of driven members to be driven by a plurality of drive members of the driving unit; a shaft whose one end portion is connected to the housing; an end effector being a clip applier that is configured to hold plural clips; a support body that is rotatably supported by the other end portion of the shaft and rotatably supports the end effector; and a plurality of driving elements that are respectively connected to the plurality of driven members to drive the end effector and the support body to rotate.

As described above, the surgical instrument according to the second aspect may include: the end effector as the clip applier that is configured to hold the plural clips; the support body that is rotatably supported by the other end portion of the shaft and rotatably supports the plurality of end effectors; and the plurality of driving elements that are respectively connected to the plurality of driven members to drive the plurality of end effectors and the support body to rotate. Therefore, the single end effector can hold the plural clips, and the number of the times for attaching the clips to the surgical instrument can be reduced. As a result, the surgery time can be shortened. Further, according to the second aspect, since the surgical instrument includes the support body, the degree of freedom of movement of the end effector can be increased as compared with a so-called multi-clip applier which can continuously apply plural clips without the support body being provided.

DETAILED DESCRIPTION

Figure 1:
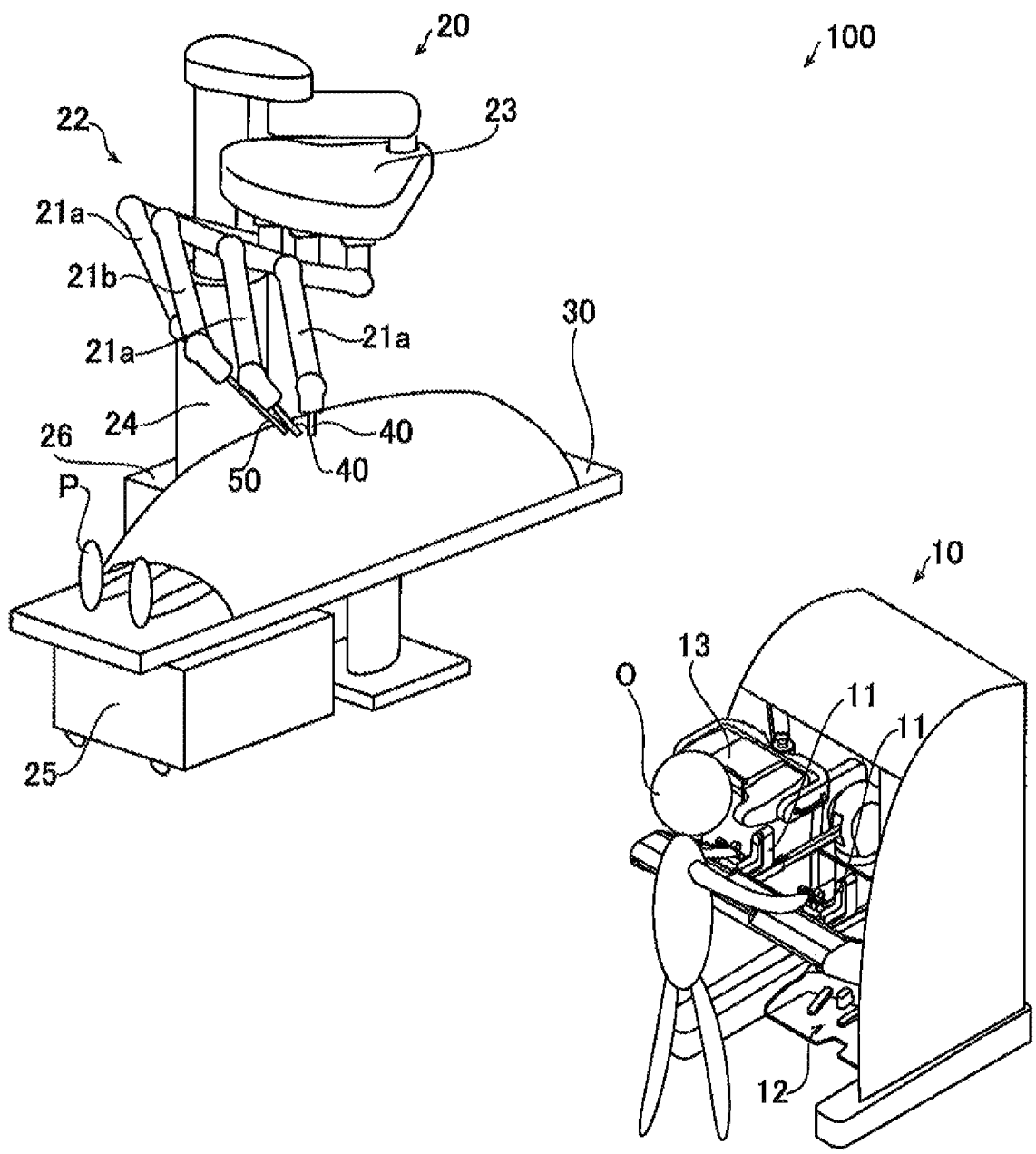
FIG. 1 is a diagram illustrating an overview of a robotic surgical system according to a first embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

First Embodiment (Configuration of Robotic Surgical System)

The configuration of a robotic surgical system 100 according to a first embodiment is described with reference to FIGS. 1 and 2.

As illustrated in FIG. 1, the robotic surgical system 100 includes a remote control apparatus 10 and a patient-side apparatus 20.

The remote control apparatus 10 is provided to remotely control medical equipment provided to the patient-side apparatus 20. When an operator O, as a surgeon, inputs an action mode instruction to be executed by the patient-side apparatus 20, to the remote control apparatus 10, the remote control apparatus 10 transmits the action mode instruction to the patient-side apparatus 20 through a controller 26. In response to the action mode instruction transmitted from the remote control apparatus 10, the patient-side apparatus 20 operates medical equipment such as surgical instruments 40, an endoscope 50, and the like, attached to robot arms 21a and 21b. This allows minimally invasive surgery.

The patient-side apparatus 20 constitutes an interface to perform a surgery for a patient P. The patient-side apparatus 20 is positioned beside an operation table 30 on which the patient P is laid. The patient-side apparatus 20 includes the plural robot arms 21a and 21b. One robot arm 21b holds the endoscope 50 while the other robot arms 21a hold the surgical instruments 40.

The robot arms 21a and 21b are commonly supported by a platform 23. Each of the robot arms 21a and 21b includes plural joints. Each joint includes a driver provided with a servo-motor and a position detector such as an encoder. The robot arms 21a and 21b are configured so that the medical equipment attached to each of the robot arms 21a and 21b is controlled by a driving signal given through the controller 26 and performs a desired movement.

The platform 23 is supported by a positioner 22 placed on the floor of an operation room. The positioner 22 includes a column 24 and a base 25. The column 24 includes an elevating shaft adjustable in the vertical direction. The base 25 includes wheels and is movable on the floor surface.

Figure 3:
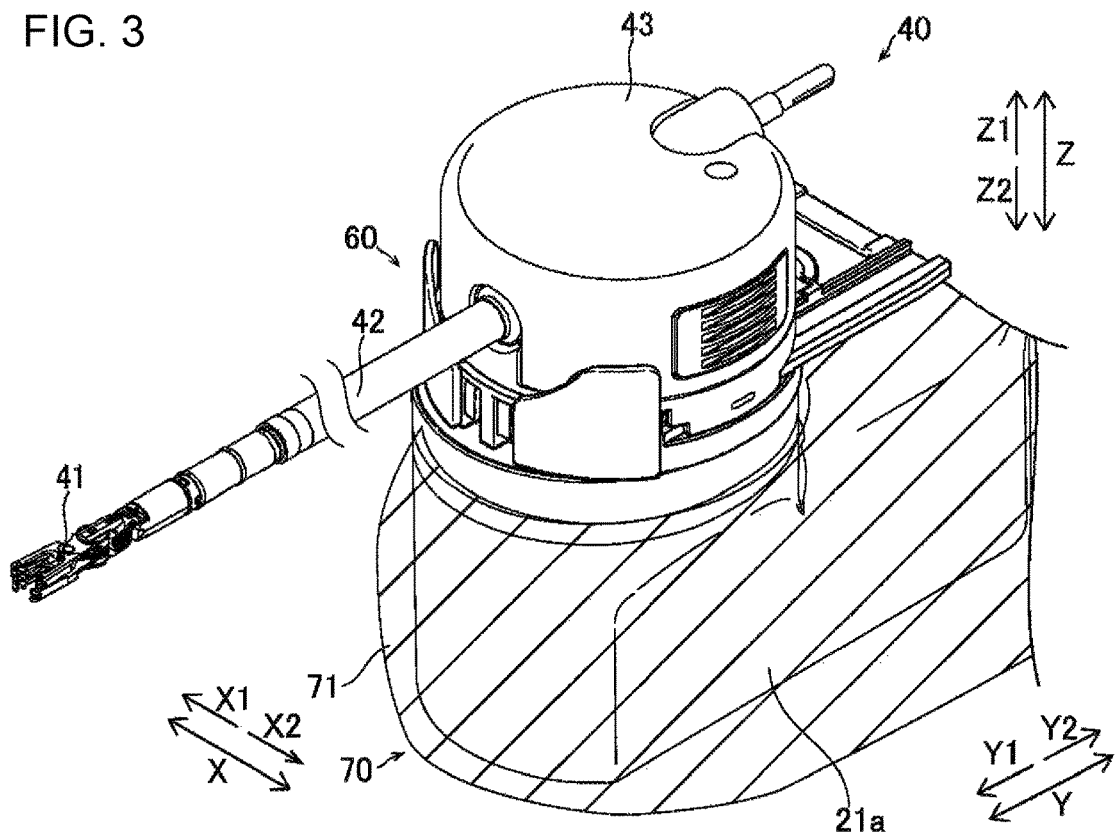
FIG. 3 is a diagram illustrating a perspective view of a state where a surgical instrument is attached to a robot arm via an adaptor according to a first embodiment.

The surgical instruments 40 as the medical equipment is detachably attached to the distal ends of the robot arms 21a. The surgical instrument 40 is a surgical instrument that is detachably connected to the robot arm 21a of the robotic surgical system 100 through an adaptor 60, as illustrated in FIG. 3. The surgical instrument 40 includes an end effector 41, and an elongate shaft 42. The end effector 41 is grasping forceps, scissors, a hook, a high-frequency knife, a snare wire, a clamp, or a stapler, for example. The end effector 41 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effectors 41 of the surgical instruments 40 are then located near a surgery site.

To the distal end of the robot arm 21b, the endoscope 50 as the medical equipment is detachably attached. The endoscope 50 captures an image in a body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21b introduces the endoscope 50 into the body of the patient P through a trocar placed on the body surface of the patient P. The endoscope 50 is then located near the surgery site.

The remote control apparatus 10 constitutes the interface with the operator O. The remote control apparatus 10 is an apparatus that allows the operator O to operate the medical equipment attached to the robot arms 21a and 21b. Specifically, the remote control apparatus 10 is configured to transmit action mode instructions which are inputted by the operator O and are to be executed by the surgical instruments 40 and endoscope 50, to the patient-side apparatus 20 through the controller 26. The remote control apparatus 10 is installed beside the operation table 30 so that the operator O can see the condition of the patient P very well while operating the remote control apparatus 10, for example. The remote control apparatus 10 may be configured to transmit action mode instructions wirelessly and installed in a room different from the operation room where the operation table 30 is installed.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object. Further the action modes may include an action to supply current to a bipolar or monopolar instrument to burn off the surgery site.

The action modes to be executed by the endoscope 50 include the position and posture of the tip of the endoscope 50 and setting of the zoom magnification, for example.

Figure 2:
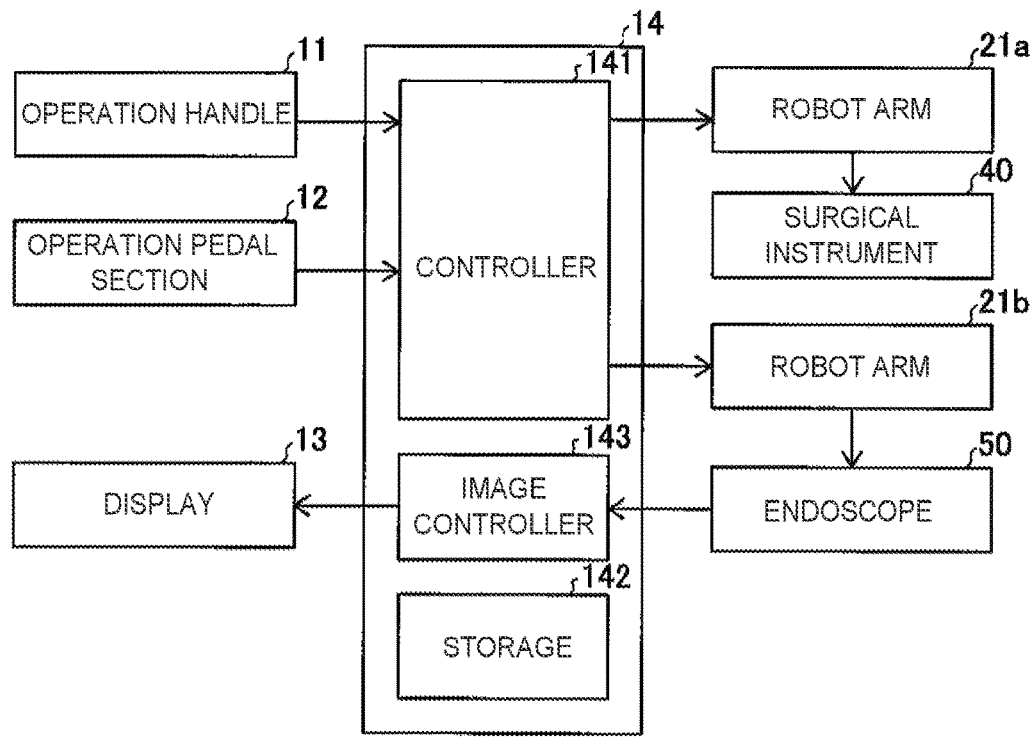
FIG. 2 is a block diagram illustrating a view of a control-related configuration of the robotic surgical system according to a first embodiment.

As illustrated in FIGS. 1 and 2, the remote control apparatus 10 includes operation handles 11, an operation pedal section 12, a display 13, and a control apparatus 14.

The operation handles 11 are provided in order to remotely operate medical equipment attached to the robot arms 21a and 21b. Specifically, the operation handles 11 accept operations by the operator O for operating the medical equipment (the surgical instruments 40 and endoscope 50). The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 10 toward the front side. The operation handles 11 are configured to move in a predetermined three-dimensional operation region. Specifically, the operation handles 11 are configured so as to move up and down, right and left, and forward and rearward.

The remote control apparatus 10 and patient-side apparatus 20 constitute a master-slave system in terms of controlling movement of the robot arms 21a and robot arm 21b. The operation handles 11 constitute an operating part on the master side in the master-slave system, and the robot arms 21a and 21b holding the medical equipment constitute an operating part on the slave side. When the operator O operates the operation handles 11, the movement of one of the robot arms 21a or 21b is controlled so that the distal end portion (the end effector 41 of the surgical instrument 40) of the robot arm 21a or the distal end portion (the endoscope 50) of the robot arm 21b moves following the movement of the operation handles 11.

The patient-side apparatus 20 controls the movement of the robot arms 21a in accordance with the set motion scaling ratio. When the motion scaling ratio is set to 1/2, for example, the end effectors 41 of the surgical instruments 40 move 1/2 of the movement distance of the operation handles 11. This allows for precise fine surgery.

The operation pedal section 12 or an operation pedal unit includes plural pedals to execute medical equipment-related functions. The plural pedals include a coagulation pedal, a cutting pedal, a camera pedal, and a clutch pedal. The plural pedals are operated by a foot of the operator O.

The coagulation pedal enables the surgical instrument 40 to coagulate a surgery site. Specifically, when the coagulation pedal is operated, voltage for coagulation is applied to the surgical instrument 40 to coagulate the surgery site. The cutting pedal enables the surgical instrument 40 to cut the surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. That is, the position and orientation of the endoscope 50 are controllable by the operation handles 11 while the camera pedal is being pressed. The endoscope 50 is controlled by using both of the right and left operation handles 11, for example. Specifically, when the operator O rotates the right and left operation handles 11 about the middle point between the right and left operation handles 11, the endoscope 50 is rotated. When the operator O presses the right and left operation handles 11 together, the endoscope 50 goes forward into the body cavity. When the operator O pulls the right and left operation handles 11 together, the endoscope 50 goes back. When the operator O moves the right and left operation handles 11 together up, down, right, or left, the endoscope 50 moves up, down, right, or left, respectively.

The clutch pedal is used to temporarily disconnect operation-related connection between the operation handles 11 and the robot arms 21a to stop movement of the surgical instruments 40. Specifically, when the clutch pedal is being pressed, the robot arms 21a of the patient-side apparatus 20 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21a. The operator O restarts the operation for the operation handles 11 around the center thereof.

The display 13 or a display unit is configured to display images captured by the endoscope 50. The display 13 includes a scope type display or a non-scope type display. The scope type display is a display that the operator O looks into. The non-scope type display is a display like an open-type display that includes a flat screen and the operator O is able to see without looking into, such as normal displays for personal computers.

When the scope type display is attached, the scope type display displays 3D images captured by the endoscope 50 attached to the robot arm 21b of the patient-side apparatus 20. When the non-scope type display is attached, the non-scope type display also displays 3D images captured by the endoscope 50 provided for the patient-side apparatus 20. The non-scope type display may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM and a RAM. The control apparatus 14 may be composed of a single controller performing centralized control or may be composed of plural controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display 13. The image controller 143 performs processing and alternations for the images when needed.

(Configurations of Surgical Instrument, Adaptor, Drape, and Robot Arm)

Figure 4:
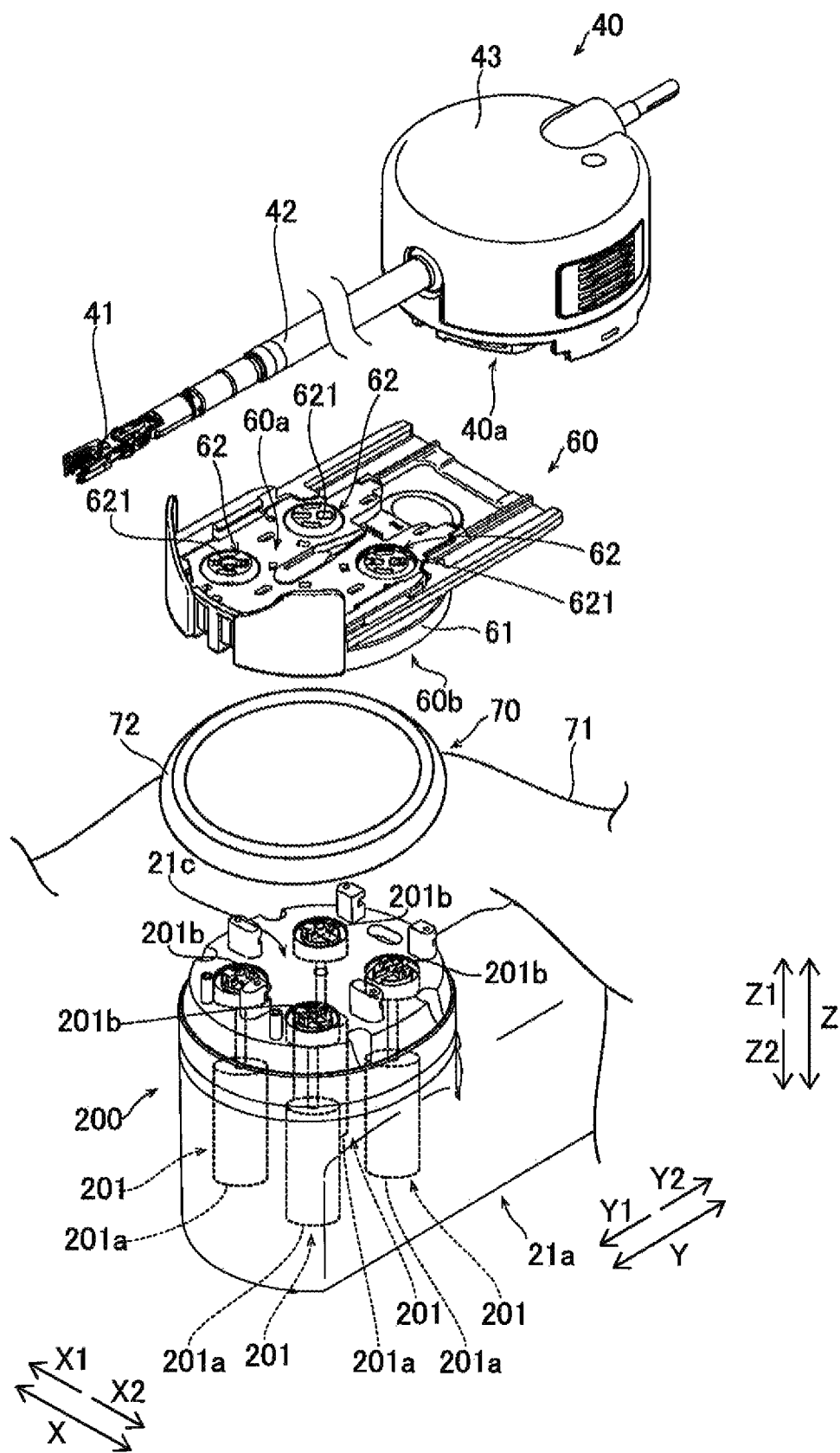
FIG. 4 is a diagram illustrating a perspective view of a state where the surgical instrument and the adaptor are detached from the robot arm according to a first embodiment.
Figure 5:
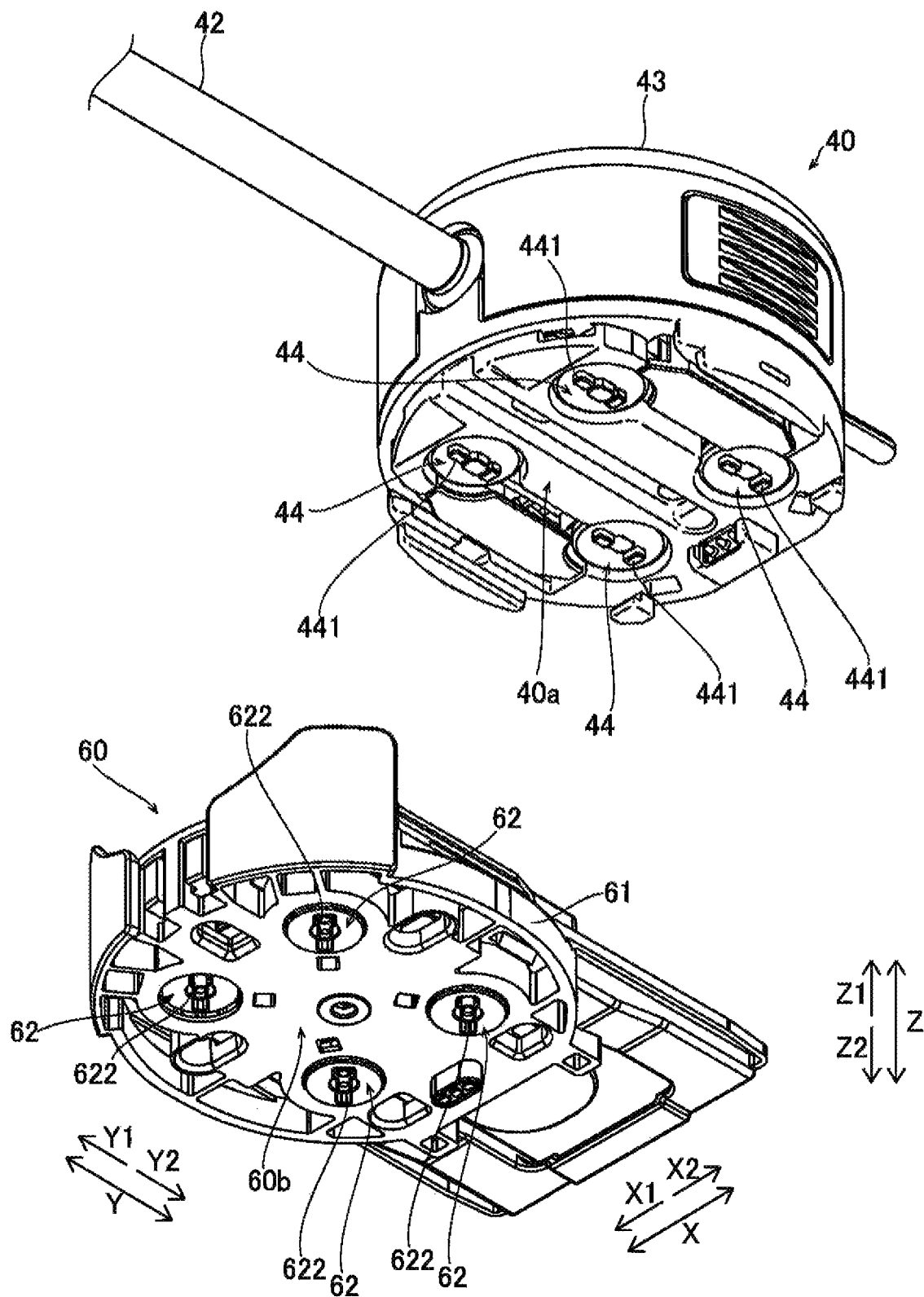
FIG. 5 is a diagram illustrating a perspective view of the adaptor and the surgical instrument according to a first embodiment as seen from below.

With reference to FIGS. 3 to 5, configurations of the surgical instrument 40, the adaptor 60, a drape 70, and the robot arm 21a according to a first embodiment are described.

As illustrated in FIGS. 3 to 5, the surgical instrument 40 is detachably connected to the robot arm 21a via the adaptor 60. The adaptor 60 is arranged between a driving unit 200 (described later) of the robot arm 21a and the surgical instrument 40. The adaptor 60 is a drape adaptor for holding the drape 70 and is to be replaced by the user after each surgery. Accordingly, the drape 70 can be held by using the adaptor 60. The drape 70 is for covering the robot arm 21a and is sterilized. The adaptor 60 is configured to put the drape 70 between the adaptor 60 and the robot arm 21a.

The surgical instrument 40 includes a connection portion 40a, serving as an attachment surface, provided on the Z2 side of the surgical instrument 40, and the connection portion 40a of the surgical instrument 40 is to be attached to the adaptor 60. The connection portion 40a is provided at a housing 43 (described later) and is attached to the robot arm 21a via the adaptor 60. The adaptor 60 includes a connection portion 60a, serving as an attachment surface, provided on the Z1 side of the adaptor 60, and the connection portion 60a of the adaptor 60 is to be attached and connected to the surgical instrument 40. The adaptor 60 includes a connection portion 60b, serving as an attachment surface, provided on the Z2 side of the adaptor 60, and the connection portion 60b of the adaptor 60 is to be attached and connected to the driving unit 200 of the robot arm 21a. The driving unit 200 of the robot arm 21a includes a connection portion 21c, serving as an attachment surface, provided on the Z1 side of the robot arm 21a, and the adaptor 60 is to be attached and connected to the connection portion 21c of the robot arm 21a.

The robot arm 21a is used in a clean area and is covered with the drape 70. In operation rooms, clean technique is used in order to prevent surgical incision sites and medical equipment from being contaminated by pathogen, foreign matters, or the like. The clean technique defines a clean area and a contaminated area, which is outside the clean area. The surgery sites are located in the clean area. Members of the surgical team, including the operator O, make sure that only sterile objects are placed in the clean area during surgery and perform sterilization for an object which is to be moved to the clean area from the contaminated area. Similarly, when the members of the surgical team including the operator O place their hands in the contaminated area, the members sterilize their hands before directly touching objects located in the clean area. Instruments used in the clean area are sterilized or are covered with sterile drape 70.

The drape 70 includes a body section 71 that covers the robot arm 21a and an attachment section 72 that is sandwiched between the driving unit 200 of the robot arm 21a and the adaptor 60. The body section 71 is made of a flexible film member. The flexible film member is made of a resin material, such as thermoplastic polyurethane and polyethylene. The body section 71 includes an opening such that the driving unit 200 of the robot arm 21a and the adaptor 60 are engageable with each other. In the opening of the body section 71, the attachment section 72 is provided so as to close the opening. The attachment section 72 is made of a resin mold member. The resin mold member is made of a resin member such as polyethylene terephthalate. The attachment section 72 is harder (less flexible) than the body section 71. The attachment section 72 includes an opening such that the driving unit 200 of the robot arm 21a and the adaptor 60 are engageable with each other. The opening of the attachment section 72 may be provided corresponding to a portion where the driving unit 200 of the robot arm 21a is engaged with the adaptor 60. The opening of the attachment section 72 may include plural openings corresponding to plural portions at which the driving unit 200 of the robot arm 21a is engaged with the adaptor 60.

The surgical instrument 40 includes a housing 43 in addition to the end effector 41 and the shaft 42. The housing 43 is configured to be attached to the driving unit 200 of the robot arm 21a via the adaptor 60. To the housing 43, one end portion (an end portion on the Z2 side, or a first end portion) of the shaft 42 is connected. The housing 43 of the surgical instrument 40 is provided with plural (four) drive members 44 to be driven by plural (four) drive members 201 of the driving unit 200 of the robot arm 21a. The plural driven members 44 are provided inside the housing 43 and are rotatable about respective rotation axes extending along the Z direction (Z axis direction). The plural driven members 44 are provided to operate (drive) the end effector 41.

Three of the plural driven members 44 are configured to be driven to rotate the end effector 41 by later-described driving elements (elongate elements) 46a, 46b, and 46c passing through the inside of the shaft 42. With this configuration, rotations of the three driven members 44 drive the driving elements 46a, 46b, and 46c to move, and movements of the driving elements (elongate elements) 46a, 46b, and 46c drive the end effector 41 to rotate. In addition, the other one of the driven members 44 is connected to the shaft 42 via gears (not illustrated). With this configuration, rotation of the one driven member 44 rotates the shaft 42, and rotation of the shaft 42 drives the end effector 41 to rotate. To transmit driving forces from the driving unit 200 of the robot arm 21a, the plural driven members 44 include fitting protrusions 441, which are engaged with later-described drive transmission members 62 of the adaptor 60. The fitting protrusions 441 protrude from the Z2-side surfaces of the respective driven members 44 toward the adaptor 60 (in the Z2 direction).

The adaptor 60 includes an adaptor main body 61 and the plural (four) drive transmission members 62 supported by the adaptor main body 61 to be rotatable about respective rotational axes extending in the Z direction with respect to the adaptor main body 61. The plural drive transmission members 62 are provided in the adaptor main body 61 to be rotatable about their rotation axes. The number (four) of the plural drive transmission members 62 provided corresponds to the number (four) of the plural driven members 44 of the surgical instrument 40. The drive transmission members 62 are configured to transmit the driving forces from the robot arm 21a to the driven members 44 of the surgical instrument 40. The drive transmission member 62 include fitting recesses 621 (see FIG. 4), which are engaged with the fitting protrusions 441 of the driven members 44 of the surgical instrument 40. The fitting recess 621 is provided at a surface of the drive transmission member 62 on the Z1 side (the surgical instruments 40 side) and is recessed from the Z1-side surface of the drive transmission member 62 toward a direction (in the Z2 direction) opposite to the surgical instruments 40 side.

The drive transmission members 62 include fitting recesses 622 (see FIG. 5), which are engaged with fitting protrusions 201b (described later) of the drive members 201 of the driving unit 200 of the robot arm 21a. The fitting recess 622 is provided at a surface of the drive transmission member 62 on the Z2 side (the robot arm 21a side) and is recessed from the Z2-side surface of the drive transmission member 62, in a direction (the Z1 direction) opposite to the robot arm 21a side.

The robot arm 21a includes the driving unit 200 (see FIG. 4) to drive the driven members 44 (see FIG. 5) of the surgical instrument 40. The driving unit 200 is configured to generate the driving forces to be applied to the driven members 44 of the surgical instrument 40. Specifically, the driving unit 200 includes the plural (four) drive members 201 (see FIG. 4) provided corresponding to the plural driven members 44 of the surgical instruments 40. Each drive member 201 includes an actuator 201a (see FIG. 4) including a motor serving as a driving source and a fitting protrusion 201b (see FIG. 4) to be rotated by the actuator 201a about a rotational axis thereof extending in the Z direction. The fitting protrusions 201b protrude from the Z2-side surfaces of the respective drive members 201 toward the adaptor 60 (in the Z1 direction).

(Detailed Configuration of Surgical Instrument)

With reference to FIGS. 6 to 9, the configuration of the surgical instrument 40 according to a first embodiment is described in detail.

Figure 6:
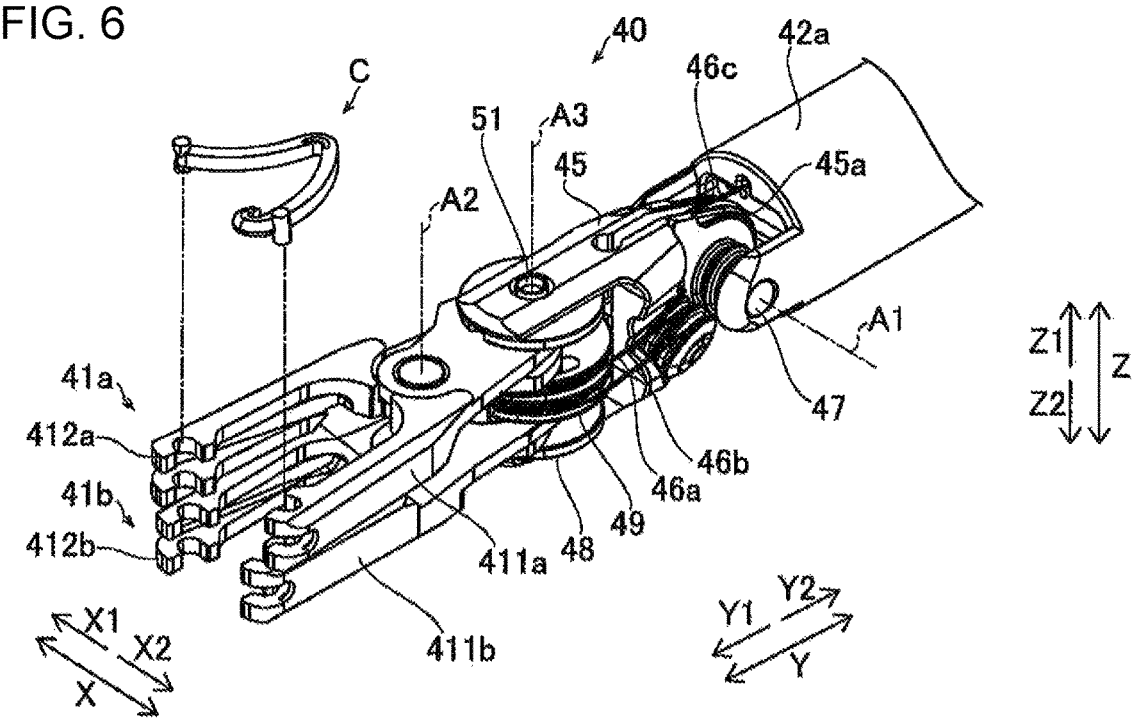
FIG. 6 is a diagram illustrating a perspective view of a configuration around an end portion of a shaft of the surgical instrument according to a first embodiment.

In a first embodiment, as illustrated FIG. 6, the surgical instrument 40 includes a plurality of end effectors 41a and 41b, that is, the above-described end effector 41 includes the plurality of end effectors 41a and 41b. The surgical instrument 40 includes a support body (clevis) 45 that is rotatably supported by the other end portion (an end portion on the Y1-side, or a second end portion) 42a of the shaft 42 and rotatably supports the plurality of end effectors 41a and 41b. The surgical instrument 40 includes the driving elements (elongate elements) 46a, 46b, and 46c connected to the plural driven members 44 (see FIG. 5) to drive the end effectors 41a and 41b and the support body 45 to rotate. With this configuration, since the single surgical instrument 40 is equipped with the plurality of end effectors 41a and 41b, it is possible to reduce the number of times the surgical instrument is inserted into and removed from the surgical site, and reduce the number of times an accessory such as the clip C is attached to the surgical instrument 40. As a result, the surgery time can be shortened. Note that the end effector 41a is an example of a first end effector. Note that the end effector 41b is an example of a second end effector.

The support body 45 is rotatably supported by the rotation shaft 47 supported on the other end portion 42a of the shaft 42. The rotational shaft 47 is provided to extend in the Z direction. The support body 45 is provided to be rotatable about a rotational axis A1 extending in the X direction. The support body 45 includes a winding portion 45a on which the driving element 46c is wound. The support body 45 is configured to be rotated about the rotational axis A1 by the driving element 46c. The support body 45 supports the plural end effectors 41a and 41b. The support body 45 is configured to be driven to rotate about the rotational axis A1 so that the rotation of the support body 45 about the rotational axis A1 drives the plural end effectors 41a and 41b to rotate about the rotational axis A1.

In a first embodiment, the driving elements (elongate elements) 46a, 46b, and 46c are wires. Therefore, with this simple structure, the end effectors 41a and 41b and the support body 45 can be driven to rotate. The driving elements 46a and 46b are configured to drive the end effectors 41a and 41b to rotate. The driving element 46c is configured to drive the support body 45 to rotate. Note that rotation drive operations of the end effectors 41a and 41b by means of the driving elements 46a and 46b are described later in detail.

In a first embodiment, the number of the end effectors is two. With this configuration, the number of the driven members 44 and the numbers of the driving elements 46a and 46b can be reduced to simplify the structure of the surgical instrument 40, compared to a case where the number of the end effectors is three or more. In a first embodiment, each of the end effectors 41a and 41b includes a clip applier which can mount a clip C thereto. That is, the surgical instrument 40 includes two clip appliers. With this configuration, the number of times the clips C are attached to the end effectors 41a and 41b of the surgical instrument 40 can be reduced by half, compared to a case where the surgical instrument 40 includes only one clip applier. Therefore, the time to be spent for attaching the clips C to the end effectors 41a and 41b can be shortened, and thus the surgery time can be shortened. Further, the surgical instrument 40 can clip a clipping target such as a blood vessel at two places (or twice), without the surgical instrument 40 being pulled out from the surgical site (inside of the body) of the patient P. Therefore, the surgery time can be shortened. Each of the end effectors 41a and 41b, serving as the clip applier, is configured to be able to attach one clip C for clipping the clipping target in the surgical site. Note that, although FIG. 6 illustrates only the clip C that is attached to the end effector 41a, the clip C is attached not only to the end effector 41a but also to the end effector 41b.

The end effector 41a (41b) includes a first jaw 411a (411b) and a second jaw 412a (412b) that can be opened and closed with respect to each other. The first jaw 411a of the end effector 41a and the first jaw 411b of the end effector 41b are disposed on one side (first side) in a direction orthogonal to the rotational axis A2 of the plural end effectors 41a and 41b. Further, the second jaw 412a of the end effector 41a and the second jaw 412b of the end effector 41b are disposed on the other side (second side) in the direction orthogonal to the rotational axis A2 of the plural end effectors 41a and 41b.

The end effector 41a (41b) is configured to sandwich the clip C between the first jaw 411a (411b) and the second jaw 412a (412b). Further, the end effector 41a (41b) is configured to clip the clipping target with the clip C by closing the first jaw 411a (411b) and the second jaw 412a (412b) with respect to each other. Further, the end effector 41a (41b) is configured to open and close by being rotated about the rotational axis A2 extending in the Z direction orthogonal in the X direction. Note that the extending direction of the rotational axis A2 of the plural end effectors 41a and 41b and the extending direction of the rotational axes A3 of the support body 45 are orthogonal to each other. With this configuration, the plural end effectors 41a and 41b can be moved in a more complicated manner (three-dimensionally), compared to a case where the direction of the rotational axis A2 of the plural end effectors 41a and 41a is substantially parallel to the direction of the rotational axis A1 of the support body 45.

Figure 7A:
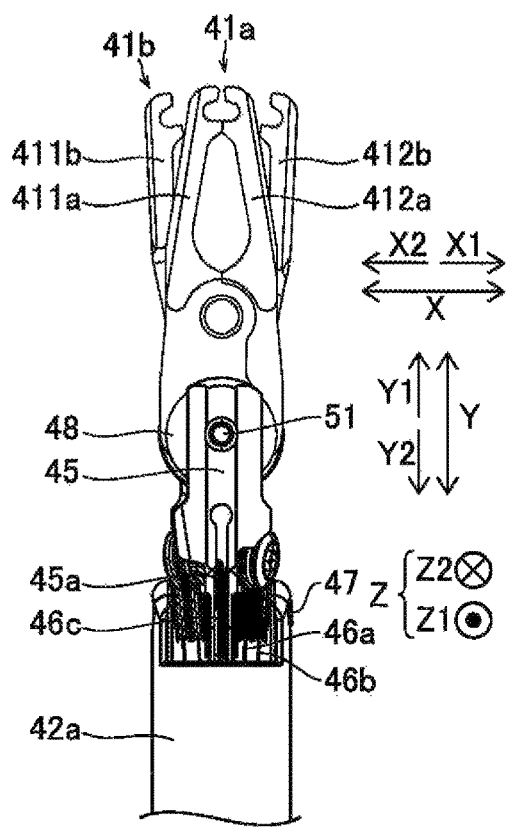
FIG. 7A is a diagram illustrating an explanatory view for explaining operations of alternatingly opening and closing plural end effectors of the surgical instrument according to a first embodiment.
Figure 7B:
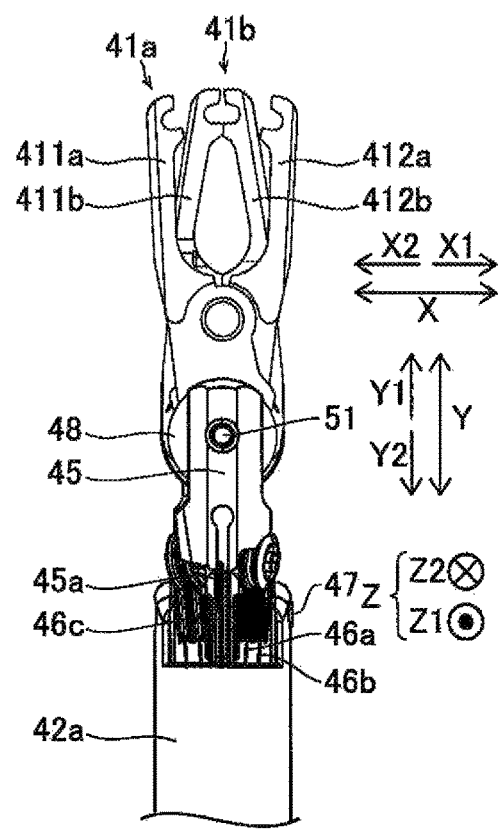
FIG. 7B is a diagram illustrating an explanatory view for explaining the operations of alternatingly opening and closing the plural end effectors of the surgical instrument according to a first embodiment.

Further, in a first embodiment, as illustrated in FIGS. 7A and 7B, the end effectors 41a and 41b are configured to be alternatingly opened and closed. In other words, the end effectors 41a and 41b are configured to be linked with each other to be moved in reverse directions from each other. With this configuration, the end effectors 41a and 41b can be moved in the reverse directions from each other and thus can perform more complexed operations, unlike a configuration where the two end effectors are opened and closed together in the same direction at the same time. For example, after the end effector 41a performs the clipping operation to a clipping target, the effector 41b can perform the clipping operation to another clipping target. In a first embodiment, the end effectors 41a and 41b are configured in such a manner that, when one of the end effectors 41a and 41b is in an opening operation, the other effector is in a closing operation, whereas when the one of the end effectors 41a and 41b is in a closing operation, the other end effector is in an opening operation.

Specifically, the plural end effectors 41a and 41b are configured in such a manner that, when the first and second jaws 411a and 412a of the end effector 41a are in the opening operation, the first and second jaws 411b and 412b of the end effector 41b are in the closing operation, whereas when the first and second jaws 411a and 412a of the end effector 41a are in the closing operation, the first and second jaws 411b and 412b of the end effector 41b are in an opening operation.

Further, the end effectors 41a and 41b are configured in such a manner that, the first jaw 411a of the end effector 41a and the second jaw 412b of the end effector 41b are rotated together, whereas the second jaw 412a of the end effector 41a and the first jaw 411b of the end effector 41b are rotated together, so that the end effectors 41a and 41b are synchronizingly moved in reverse directions from each other. With this configuration, the structure for rotationally driving the end effectors 41a and 41b can be simplified and the operation for rotationally driving the end effectors 41a and 41b can be simplified, compared to a case where the first jaw 411a and the second jaw 412a of the end effector 41a and the first jaw 411b and the second jaw 412b of the end effector 41b are rotated independently from each other.

Specifically, when the first jaw 411a of the end effector 41a and the second jaw 412b of the end effector 41b are rotated in a first rotational direction about the rotational axis A2 while the second jaw 412a of the end effector 41a and the first jaw 411b of the end effector 41b are rotated in a second rotational direction opposite to the first rotational direction, the end effector 41a is driven in the closing operation and the end effector 41b is driven in the opening operation. Similarly, when the first jaw 411a of the end effector 41a and the second jaw 412b of the end effector 41b are rotated in the second rotational direction, while the second jaw 412a of the end effector 41a and the first jaw 411b of the end effector 41b are rotated in the first rotational direction, the end effector 41a is driven in the opening operation and the end effector 41b is driven in the closing operation.

Figure 8:
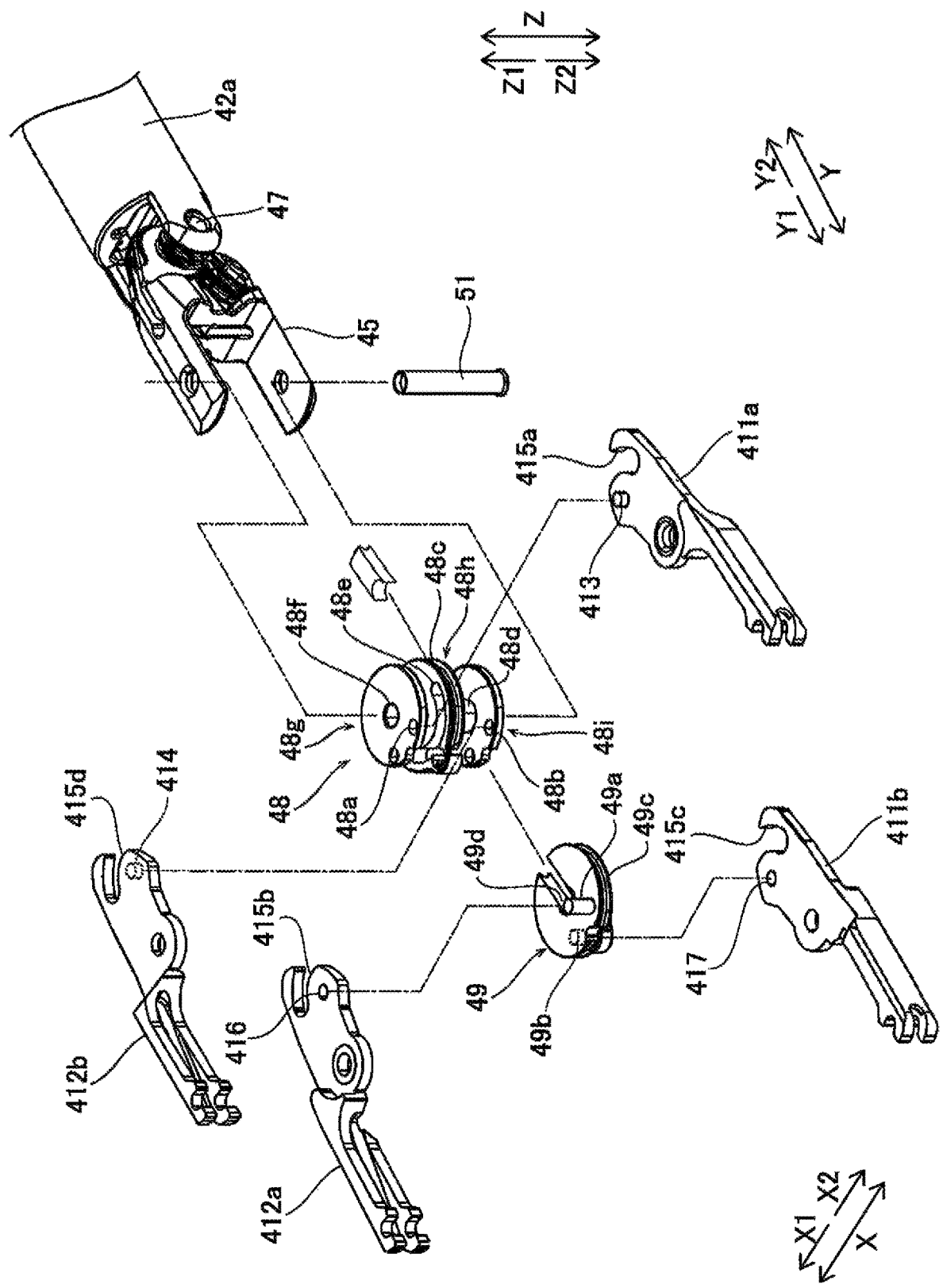
FIG. 8 is a diagram illustrating an exploded perspective view of a configuration around the end portion of the shaft of the surgical instrument according to a first embodiment.

In a first embodiment, as illustrated in FIGS. 6 to 8, the plural end effectors 41a and 41b of the surgical instrument 40 includes pulley parts 48 and 49 to rotate the end effectors 41a and 41b in a linked manner. With this configuration, the pulley parts 48 and 49 to rotate the end effectors 41a and 41b can be shared, and thus the structure of the surgical instrument 40 can be simplified. The pulley part 48 is configured to be engaged with the first jaw 411a of the end effector 41a and with the second jaw 412b of the end effector 41b. Specifically, the pulley part 48 is configured to support both the first jaw 411a of the end effector 41a and the second jaw 412b of the end effector 41b and thus rotate together the first jaw 411a of the end effector 41a and the second jaw 412b of the end effector 41b. The pulley part 49 is configured to be engaged with the second jaw 412a of the end effector 41a and with the first jaw 411b of the end effector 41b. Specifically, the pulley part 49 is configured to support both the second jaw 412a of the end effector 41a and the first jaw 411b of the end effector 41b and thus rotate together the second jaw 412a of the end effector 41a and the first jaw 411b of the end effector 41b. With this, the first jaw 411a of the end effector 41a and the second jaw 412b of the end effector 41b can be rotated together by means of the pulley part 48, and the second jaw 412a of the end effector 41a and the first jaw 411b of the end effector 41b can be rotated together by means of the pulley part 49. Note that the pulley part 48 is an example of a first pulley part. The pulley part 49 is an example of a second pulley part.

Figure 9:
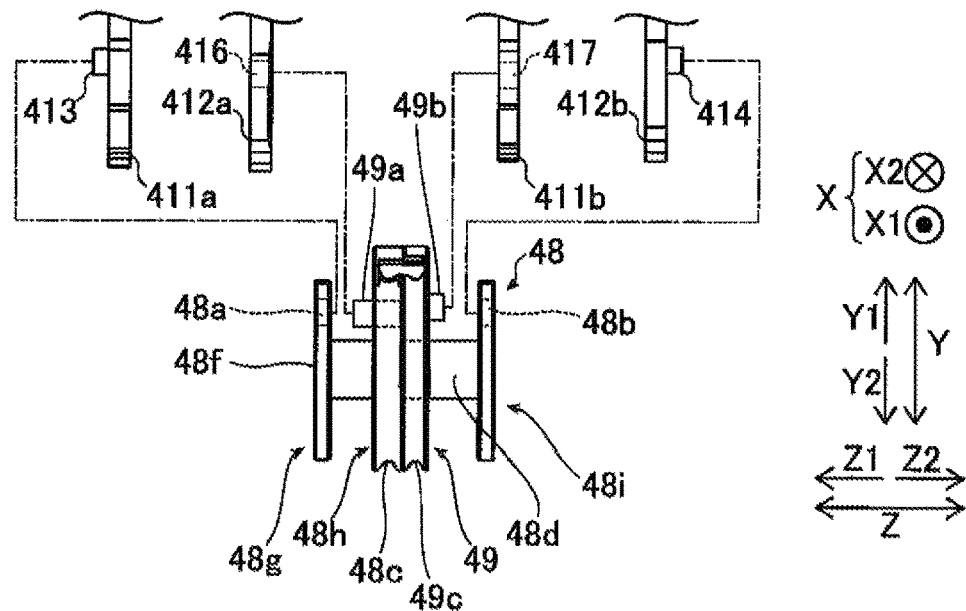
FIG. 9 is a diagram illustrating an explanatory view for explaining connection between the plural end effectors and plural pulley parts according to a first embodiment.

As illustrated in FIGS. 8 and 9, the pulley part 48 includes a first engagement portion 48a, a second engagement portion 48b, a pulley groove 48c, a shaft portion 48d, an opening 48e, and a through hole 48f. The first engagement portion 48a is configured to be engaged with an engagement portion 413 of the first jaw 411a of the end effector 41a. The first engagement portion 48a is configured as a through hole extending in the Z direction. The engagement portion 413 of the first jaw 411a is configured as a convex part (a projection) extending in the Z1 direction. The second engagement portion 48b is configured to be engaged with an engagement portion 414 of the second jaw 412b of the end effector 41b. The second engagement portion 48b is configured as a through hole extending in the Z direction. The engagement portion 414 of the second jaw 412b is configured as a convex part (a projection) extending in the Z2 direction. The pulley groove 48c is provided on which the driving element 46a (see FIG. 6) is wound. The pulley part 48 is driven to rotate by the driving element 46a passing in the pulley groove 48c so that the first jaw 411a of the end effector 41a and the second jaw 412b of the end effector 41b, which are respectively engaged with the first engagement portion 48a and the second engagement portion 48b, are rotated about the rotational axis A2 (see FIG. 6).

The shaft portion 48d is provided extending in the Z direction. The shaft portion 48d is configured to be attached to the pulley part 49. Further, the first jaw 411a and the second jaw 412a of the end effector 41a and the first jaw 411b and the second jaw 412b of the end effector 41b are provided with notch portions (removed portions) 415a, 415b, 415c, and 415d, respectively, to avoid interferences with the shaft portion 48d. With this configuration, it is possible to prevent the shaft portion 48d of the pulley 48 from interfering with the end effectors 41a and 41b when rotating the end effectors 41a and 41b. The opening 48e is provided to insert a first engagement portion 49a (described later) of the pulley part 49 therein. The opening 48e is formed in an arc shape so as not to hider movements of the first engagement portion 49a when the pulley 49 is rotated. The through hole 48f is provided to insert the rotational shaft 51 therein. The rotational shaft 51 is provided to extend in the Z direction orthogonal to the X direction. The pulley part 48 is rotatably supported by the rotational shaft 51 supported on the support body 45. The pulley part 48 is provided to be rotatable about the rotation axis A3 (see FIG. 6) extending in the Z direction.

The pulley part 48 includes plural (three) disc portions 48g, 48h, and 48i each having a substantially circular shape as seen in the Z direction. The disc portions 48g, 48h, and 48i are arranged in that order from the Z1 side toward the Z2 side. The disc portion 48g is provided with the first engagement portion 48a that passes through the disc portion 48g in the Z direction. The disc portion 48h is provided with a pulley groove 48c extending along an outer circumference of the disc portion 48*h*. The disc portion 48*h* is provided with the opening 48*e* penetrating through the disc portion 48*h* in the Z direction. The disc portion 48*i* is provided with the second engagement portion 48*b* that penetrates through the disc portion 48*i* in the Z direction.

The disc portions 48*g*, 48*h*, and 48*i* are connected to each other with the shaft portion 48*d*. Specifically, the shaft portion 48*d* includes a first section provided between the disc portions 48*g* and 48*h* and connecting the disc portions 48*g* and 48*h* and a second section provided between the disc portions 48*h* and 48*i* and connecting the disc portions 48*h* and 48*i*. The pulley part 49 is configured to be attached to the second section of the shaft portion 48*d*. That is, the pulley part 49 is provided between the disc portion 48*h* and 48*i* in the Z direction. The through hole 48*f* is provided to penetrate through the disc portion 48*g*, the first section of the shaft portion 48*d*, the disc portion 48*h*, the second section of the shaft portion 48*d*, and the disc portion 48*i* in that order from the Z1 side toward the Z2 side.

The pulley part 49 is a disc-shaped member having a substantially circular shape as seen along the Z direction. The pulley part 49 includes a first engagement portion 49*a*, a second engagement portion 49*b*, a pulley groove 49*c*, and a third engagement portion 49*d*. The first engagement portion 49*a* is configured to be engaged with an engagement portion 416 of the second jaw 412*a* of the end effector 41*a*. Specifically, the first engagement portion 49*a* is configured to be engaged with an engagement portion 416 of the second jaw 412*a* of the end effector 41*a* in a state where the first engagement portion 49*a* is inserted in the opening 48*e* of the pulley part 48. The first engagement portion 49*a* is configured as a convex part (a projection or a pin) extending in the Z1 direction. The engagement portion 416 is configured as a through hole extending in the Z direction. The second engagement portion 49*b* is configured to be engaged with an engagement portion 417 of the first jaw 411*b* of the end effector 41*b*. The second engagement portion 49*b* is configured as a convex part (a projection or a pin) extending in the Z2 direction. The engagement portion 417 is configured as a through hole extending in the Z direction. The pulley groove 49*c* is provided on which the driving element 46*b* (see FIG. 6) is wound. The pulley part 49 is driven to rotate by the driving element 46*b* passing in the pulley groove 49*c* so that the second jaw 412*a* of the end effector 41*a* and the first jaw 411*b* of the end effector 41*b*, which are respectively engaged with the first engagement portion 49*a* and the second engagement portion 49*b*, are rotated about the rotational axis A2 (see FIG. 6).

The third engagement portion 49*d* is a notch (or a recess portion) to be engaged with the shaft portion 48*d* of the pulley part 48. The pulley part 49 is configured to be rotatably supported by the shaft portion 48*d* of the pulley part 48 in a state where the third engagement portion 49*d* is engaged with the shaft portion 48*d* of the pulley part 48. The pulley part 49 is provided to be rotatable about the rotation axis A3 (see FIG. 6) extending in the Z direction. The pulley part 48 and the pulley part 49 are configured to rotate about the common rotational axis A3.

(Opening and Closing Operation of End Effector)

Next, opening and closing operations of the end effectors 41*a* and 41*b* are explained with reference to FIGS. 6 and 7.

As illustrated in FIGS. 6 and 7, in order to close the end effector 41*a* and open the end effector 41*b*, the pulley part 48 is rotated in a third rotational direction about the rotational axis A3 by means of the driving element 46*a*, while the pulley part 49 is rotated in a fourth rotational direction opposite to the third rotational direction by means of the driving element 46*b*. With this, the first jaw 411*a* of the end effector 41*a* and the second jaw 412*b* of the end effector 41*b*, which are engaged with the pulley part 48, are rotated in the first rotational direction about the rotational axis A2, while the second jaw 412*a* of the end effector 41*a* and the first jaw 411*b* of the end effector 41*b*, which are engaged with the pulley part 49, are rotated in the second rotational direction opposite to the first rotational direction. As a result, the end effector 41*a* is closed and the end effector 41*b* is opened. Note that, in a first embodiment, the first rotational direction and the third rotational direction about the respective rotational axes are the same rotational direction (e.g., the clockwise direction in FIG. 7A), and the second rotational direction and the fourth rotational direction about the respective rotational axes are the same rotational direction (e.g., the counterclockwise direction in FIG. 7A).

Further, in order to open the end effector 41*a* and close the end effector 41*b*, the pulley part 48 is rotated in the fourth rotational direction by means of the driving element 46*a*, while the pulley part 49 is rotated in the third rotational direction by means of the driving element 46*b*. With this, the first jaw 411*a* of the end effector 41*a* and the second jaw 412*b* of the end effector 41*b*, which are engaged with the pulley part 48, are rotated in the second rotational direction, while the second jaw 412*a* of the end effector 41*a* and the first jaw 411*b* of the end effector 41*b*, which are engaged with the pulley part 49, are rotated in the first rotational direction. As a result, the end effector 41*a* is opened and the end effector 41*b* is closed. As a result, the plural end effectors 41*a* and 41*b* are alternatingly opened and closed.

[First and Second Modifications of First Embodiment]

Next, first and second modifications of a first embodiment are explained with reference to FIGS. 10A and 10B. In first and second modifications of a first embodiment, examples are described in which end effectors, types of which are different from that of a first embodiment, are attached. The configurations in a first and second modifications same as those of a first embodiment are designated by the same reference numerals in the drawings, and the description thereof may be omitted for avoid redundancy.

Figure 10A:
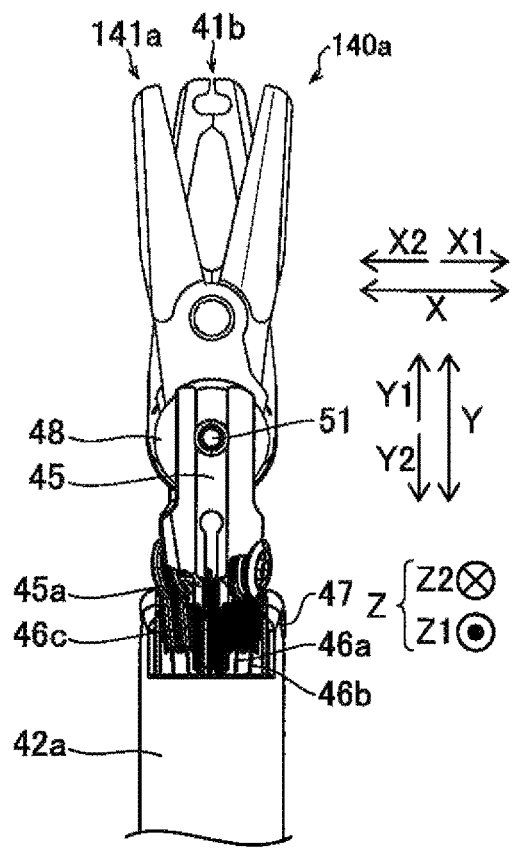
FIG. 10A is a diagram illustrating a view of a surgical instrument according to a first modification of a first embodiment.

In a first modification of a first embodiment, as illustrated in FIG. 10A, a surgical instrument 140*a* is equipped with an end effector 141*a* instead of the end effector 41*a* of a first embodiment. The end effector 141*a* is scissors that cut a cutting target such as a blood vessel in the surgical site. That is, the end effectors 141*a* and 141*b* according to a first modification include the scissors and the clip applier, respectively. With this configuration, the surgical instrument 140*a* can clip and then cut the cutting target such as a blood vessel, without the surgical instrument 140*a* being pulled out from the surgical site. As a result, the number of times the surgical instrument 140*a* is inserted into and removed from the surgery site can be reduced by half, compared to a case where the surgical instrument 140*a* is equipped with only one end effector. Therefore, the surgery time can be shortened.

Figure 10B:
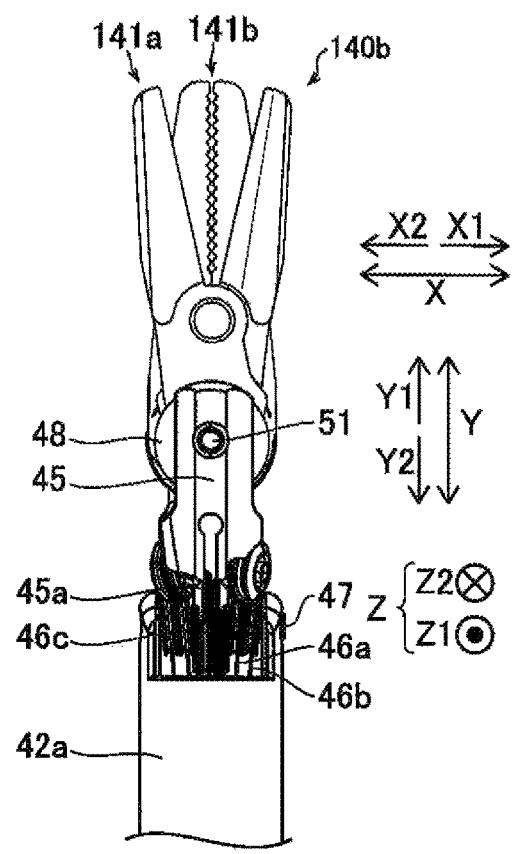
FIG. 10B is a diagram illustrating a view of a surgical instrument according to a second modification of a first embodiment.

In a second modification of a first embodiment, as illustrated in FIG. 10B, a surgical instrument 140*b* is equipped with an end effector 141*b* instead of the end effector 41*b* of a first modification of a first embodiment. The end effector 141*b* is a needle holder that holds a needle or an organ in the surgical site. That is, the end effectors 141*a* and 141*b* according to a second modification include the scissors and the needle holder, respectively. With this configuration, the surgical instrument 140*a* can cut and then suture the cut part with a needle, without the surgical instrument 140*a* being pulled out from the surgical site. As a result, the number of times the surgical instrument 140b is inserted into and removed from the surgery site can be reduced by half, compared to a case where the surgical instrument 140b is equipped with only one end effector. Therefore, the surgery time can be shortened.

Note that the other configurations in the first and second modifications are same as those in a first embodiment described above.

Second Embodiment

Next, a second embodiment is described with reference to FIGS. 11 and 12. In a second embodiment, unlike a first embodiment described above in which the plural end effectors are configured to be opened and closed in the linked manner, an example in which plural end effectors are configured to be opened or closed independently from each other. The configurations in a second embodiment same as those of a first embodiment are designated by the same reference numerals in the drawings, and the description thereof may be omitted for avoid redundancy.

Figure 11:
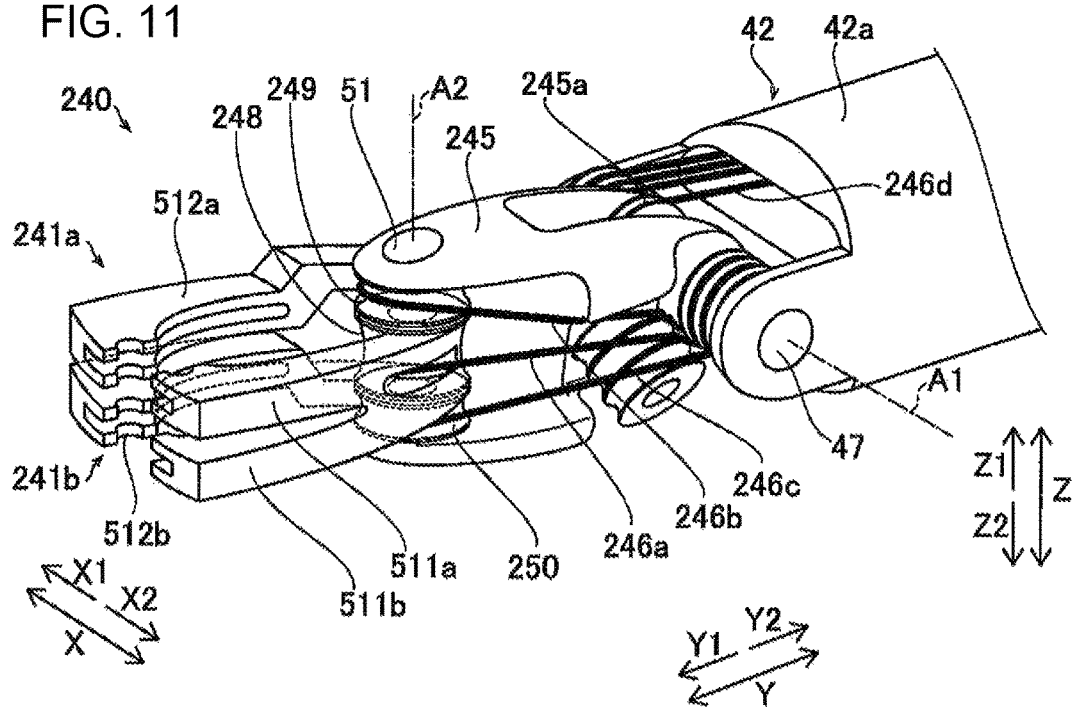
FIG. 11 is a diagram illustrating a perspective view of a configuration around an end portion of a shaft of the surgical instrument according to a second embodiment.

A surgical instrument 240 of a second embodiment is different from the surgical instrument 40 of a first embodiment described above in that the surgical instrument 240 includes plural end effectors 241a and 241b, a support body 245, and plural driving elements 246a, 246b, 246c and 246d, as illustrated in FIG. 11. Note that the end effector 241a is an example of a first end effector. Note that the end effector 241b is an example of a second end effector.

The support body 245 is rotatably supported by the rotation shaft 47 supported on the other end portion 42a of the shaft 42. The support body 245 is provided to be rotatable about a rotational axis A1 extending in the X direction. The support body 245 includes a winding portion 245a on which the driving element 246d is wound. The support body 245 is configured to be rotated about the rotational axis A1 by the driving element 246b. The support body 245 supports the plural end effectors 241a and 241b. The support body 245 is configured to be driven to rotate about the rotational axis A1 so that the rotation of the support body 245 about the rotational axis A1 drives the plural end effectors 241a and 241b to rotate about the rotational axis A1.

The plural driving elements (elongate elements) 246a, 246b, 246c, and 246d are wires. The driving elements 246a, 246b, and 246c are configured to drive the end effectors 241a and 241b to rotate. The driving element 246d is configured to drive the support body 245 to rotate. Note that rotation drive operations of the plural end effectors 241a and 241b by means of the driving elements 246a, 246b, and 246c are described later in detail.

Each of the plural end effectors 241a and 241b includes a clip applier which can mount the clip C thereto. That is, the surgical instrument 240 includes two clip appliers. Each of the end effectors 241a and 241b, serving as the clip applier, is configured to be able to attach one clip C (see FIG. 6) for clipping the clipping target in the surgical site.

The end effector 241a (241b) includes a first jaw 511a (511b) and a second jaw 512a (512b) that can be opened and closed with respect to each other. The first jaw 511a of the end effector 241a and the first jaw 511b of the end effector 241b are disposed on one side in the direction orthogonal to the rotational axis A2 of the plural end effectors 241a and 241b. Further, the second jaw 512a of the end effector 241a and the second jaw 512b of the end effector 241b are disposed on the other side in the direction orthogonal to the rotational axis A2 of the plural end effectors 241a and 241b.

The end effector 241a (241b) is configured to sandwich the clip C between the first jaw 511a (511b) and the second jaw 512a (512b). Further, the end effector 241a (241b) is configured to clip the clipping target with the clip C by closing the first jaw 511a (511b) and the second jaw 512a (512b) with respect to each other. Further, the end effector 241a (241b) is configured to open and close by being rotated about the rotational axis A2 extending in the Z direction orthogonal in the X direction.

Further, in a second embodiment, the second jaw 512a of the end effector 241a and the second jaw 512b of the end effector 241b are provided independently from each other, whereas the first jaw 511a of the end effector 241a and the first jaw 511b of the end effector 241b are provided integrally with each other.

Figure 12:
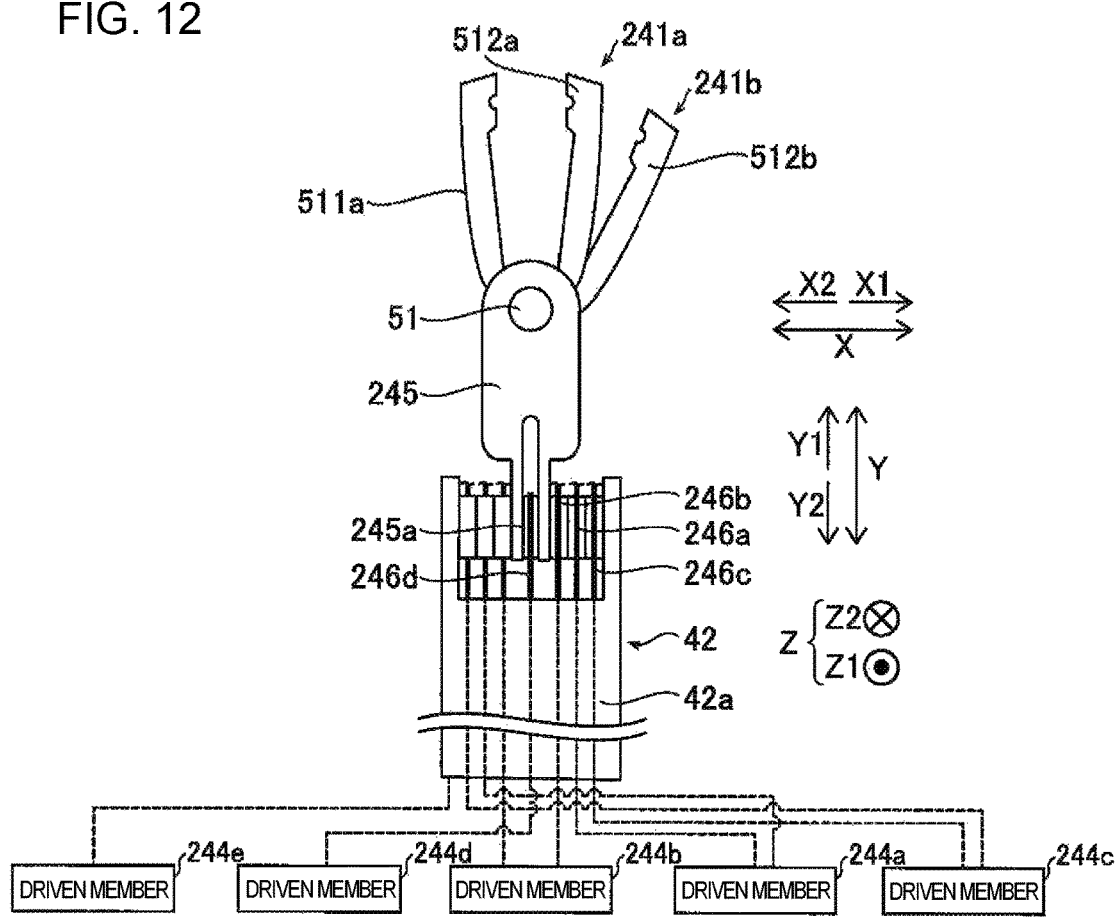
FIG. 12 is a diagram illustrating an explanatory view for explaining operations of independently opening and closing plural end effectors of the surgical instrument independently according to a second embodiment.

Further, in a second embodiment, as illustrated in FIGS. 11 and 12, the plural end effectors 241a and 241b are configured to be operated (operated or closed) independently from each other, unlike a first embodiment described above. With this configuration, the end effectors 241a and 241b can be independently operated from each other and thus can perform more complicated operations, compared to the case where the plural end effectors are configured to be simultaneously operated like the first embodiment. For example, after the end effector 241a performs the clipping operation to a clipping target, the end effector 241b can perform the clipping operation to another clipping target.

Further, in a second embodiment, the end effectors 241a and 241b are configured in such a manner that, the second jaw 512a of the end effector 241a and the second jaw 512b of the end effector 241b are rotated independently from each other, whereas the first jaw 511a of the end effector 241a and the first jaw 511b of the end effector 241b are rotated together, so that the end effectors 241a and 241b can be opened and closed independently from each other. With this configuration, the end effectors 241a and 241b can be opened and closed independently from each other, while the structure for rotationally driving the end effectors 241a and 241b can be simplified compared to a case where the first jaw 511a and the second jaw 512a of the end effector 241a and the first jaw 511b and the second jaw 512b of the end effector 241b are all rotated independently from one another.

Specifically, when the first jaw 511a of the end effector 241a and the first jaw 511b of the end effector 241b are rotated in the first rotational direction about the rotational axis A2, while the second jaw 512a of the end effector 241a is rotated in the second rotational direction opposite to the first rotational direction, the end effector 241a is driven to be closed. To the contrary, when the first jaw 511a of the end effector 241a and the first jaw 511b of the end effector 241b are rotated in the second rotational direction, while the second jaw 512a of the end effector 241a is rotated in the first rotational direction, the end effector 241a is driven to be opened. Similarly, when the first jaw 511a of the end effector 241a and the first jaw 511b of the end effector 241b are rotated in the first rotational direction, while the second jaw 512b of the end effector 241b is rotated in the second rotational direction, the end effector 241b is driven to be closed. To the contrary, when the first jaw 511a of the end effector 241a and the first jaw 511b of the end effector 241b are rotated in the second rotational direction, while the second jaw 512b of the end effector 241b is rotated in the first rotational direction, the end effector 241b is driven to be opened.

In a second embodiment, the plural end effectors 241a and 241b of the surgical instrument 240 include pulley parts 248, 249, and 250. The pulley parts 248, 249, and 250 are rotatably supported by the rotational shaft 51 supported on the support body 245. The pulley parts 248, 249, and 250 are examples of a first pulley part, a second pulley part, and a third pulley part, respectively.

The pulley part 248 is provided integrally with the first jaw 511*a* of the end effector 241*a* and the first jaw 511*b* of the end effector 241*b*. The pulley part 248 is configured to rotate the first jaw 511*a* of the end effector 241*a* and the first jaw 511*b* of the end effector 241*b* together. The pulley part 248 is provided with a pulley groove on which the driving element 246*a* is wound. The pulley part 248 is driven to rotate by the driving element 246*a* passing in the pulley groove, so that the first jaw 511*a* of the end effector 241*a* and the first jaw 511*b* of the end effector 241*b* are rotated about the rotational axis A2 (see FIG. 11).

The pulley part 249 is provided integrally with the second jaw 512*a* of the end effector 241*a*. The pulley part 249 is configured to rotate the second jaw 512*a* of the end effector 241*a*. The pulley part 249 is provided with a pulley groove on which the driving element 246*b* is wound. The pulley part 249 is driven to rotate by the driving element 246*b* passing in the pulley groove, so that the second jaw 512*a* of the end effector 241*a* is rotated about the rotational axis A2 (see FIG. 11).

The pulley part 250 is provided integrally with the second jaw 512*b* of the end effector 241*b*. The pulley part 250 is configured to rotate the second jaw 512*b* of the end effector 241*b*. The pulley part 250 is provided with a pulley groove on which the driving element 246*c* is wound. The pulley part 250 is driven to rotate by the driving element 246*c* passing in the pulley groove, so that the second jaw 512*b* of the end effector 241*b* is rotated about the rotational axis A2 (see FIG. 11). In a second embodiment, it is configured such that the first and second jaws 511*a* and 512*a* of the end effector 241*a*, the first and second jaws 511*b* and 512*b* of the end effector 241*b*, and the pulley parts 248, 249, and 250 are all rotated about the common rotational axis A2.

In a second embodiment, the surgical instrument 240 includes five driven members 244*a*, 244*b*, 244*c*, 244*d* and 244*e* as illustrated in FIG. 12, unlike the first embodiment. Note that, although detailed explanation is omitted to avoid redundancies, the number of the drive transmission members provided is five and the number of the drive members provided is five. The driven member 244*a* is configured to drive the pulley part 248 to rotate. The driven member 244*a* is connected via the driving element 246*a* to the pulley part 248. The driven member 244*b* is configured to drive the pulley part 249 to rotate. The driven member 244*b* is connected via the driving element 246*b* to the pulley part 249. The driven member 244*c* is configured to drive the pulley part 250 to rotate. The driven member 244*c* is connected via the driving element 246*c* to the pulley part 250. The driven member 244*d* is configured to drive the support body 245 to rotate. The driven member 244*d* is connected via the driving element 246*c* to the support body 245. The driven member 244*e* is configured to drive the shaft 42 to rotate. The driven member 244*e* is connected to the shaft 42 through gears (not illustrated). Note that the driven members 244*a*, 244*b*, 244*c*, 244*d* and 244*e* are examples of a first driven member, a second driven member, a third driven member, a fourth driven member, and a fifth driven member, respectively.

(Opening and Closing Operation of End Effector)

Next, opening and closing operations of the end effectors 241*a* and 241*b* are explained with reference to FIGS. 11 and 12.

As illustrated in FIGS. 11 and 12, in order to close the end effector 41*a*, the pulley part 248 is rotated in a first rotational direction about the rotational axis A2 by means of the driving element 246*a*, while the pulley part 249 is rotated in a second rotational direction opposite to the first rotational direction by means of the driving element 246*b*. With this operation, the first jaw 511*a* of the end effector 241*a* and the first jaw 511*b* of the end effector 241*b* are rotated together with the pulley part 278 in the first rotational direction, and the second jaw 512*a* of the end effector 241*a* is rotated together with the pulley part 249 in the second rotational direction. As a result, the end effector 241*a* is driven to be closed.

Further, in order to open the end effector 241*a*, the pulley part 248 is rotated in the second rotational direction about the rotational axis A2 by means of the driving element 246*a*, while the pulley part 249 is rotated in the first rotational direction by means of the driving element 246*b*. With this operation, the first jaw 511*a* of the end effector 241*a* and the first jaw 511*b* of the end effector 241*b* are rotated together with the pulley part 278 in the second rotational direction, and the second jaw 512*a* of the end effector 241*a* is rotated together with the pulley part 249 in the first rotational direction. As a result, the end effector 241*a* is driven to be opened.

Further, in order to close the end effector 241*b*, the pulley part 248 is rotated in the first rotational direction by means of the driving element 246*a*, while the pulley part 250 is rotated in the second rotational direction by means of the driving element 246*c*. With this operation, the first jaw 511*a* of the end effector 241*a* and the first jaw 511*b* of the end effector 241*b* are rotated together with the pulley part 278 in the first rotational direction, and the second jaw 512*b* of the end effector 241*b* is rotated together with the pulley part 250 in the second rotational direction. As a result, the end effector 241*b* is driven to be closed.

Further, in order to open the end effector 241*b*, the pulley part 248 is rotated in the second rotational direction about the rotational axis A2 by means of the driving element 246*a*, while the pulley part 250 is rotated in the first rotational direction by means of the driving element 246*c*. With this operation, the first jaw 511*a* of the end effector 241*a* and the first jaw 511*b* of the end effector 241*b* are rotated together with the pulley part 278 in the second rotational direction, and the second jaw 512*b* of the end effector 241*b* is rotated together with the pulley part 250 in the first rotational direction. As a result, the end effector 241*b* is driven to be opened. Therefore, the plural end effectors 241*a* and 241*b* are independently opened and closed.

Note that the other features of the configuration in the second embodiment are similar to the above first embodiment.

Third Embodiment

Next, a third embodiment is described with reference to FIGS. 13 and 14. Unlike first and second embodiments described above in which the surgical instrument includes the plural end effectors, in a third embodiment, an example in which a surgical instrument includes one end effector that can hold plural clips is described. The configurations in a third embodiment same as those of a first embodiment are designated by the same reference numerals in the drawings, and the description thereof may be omitted for avoid redundancy.

A surgical instrument 340 of a third embodiment is different from the surgical instrument 40 of a first embodiment described above, in that the surgical instrument 340 includes an end effector 341.

In a third embodiment, the surgical instrument includes only one end effector 341, that is, the number of the end effector 341 is one. The end effector 341 is configured as a clip applier which can mount a clip C (see FIG. 6) thereto. The end effector 341 is configured to mount (hold) plural (two) clips C (see FIG. 6). Therefore, the single end effector 341 can hold plural clips C, and the number of the times for attaching the clips C to the surgical instrument 40 can be reduced. As a result, the surgery time can be shortened. Further, since the surgical instrument 340 includes the support body 45 as in a first embodiment described above, the degree of freedom of movement of the end effector 341 can be increased as compared with a so-called multi-clip applier which can continuously apply a plurality of clips C without the support body 45 being provided.

Figure 13:
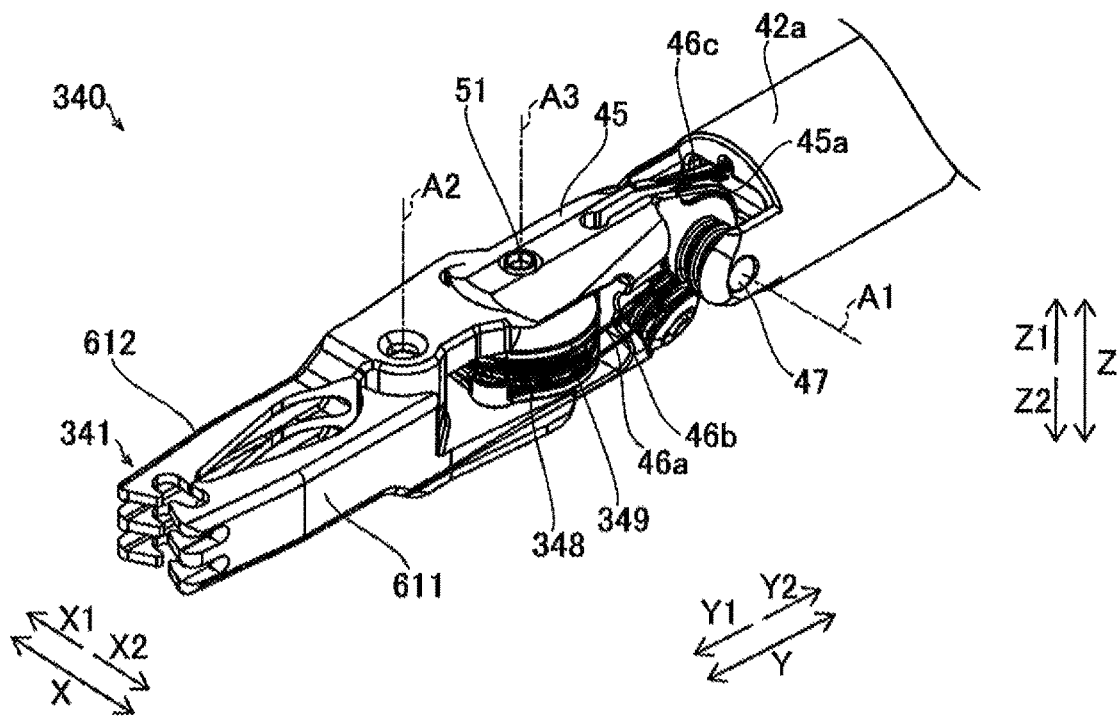
FIG. 13 is a diagram illustrating a perspective view of a configuration around an end portion of a shaft of a surgical instrument according to a third embodiment.
Figure 14:
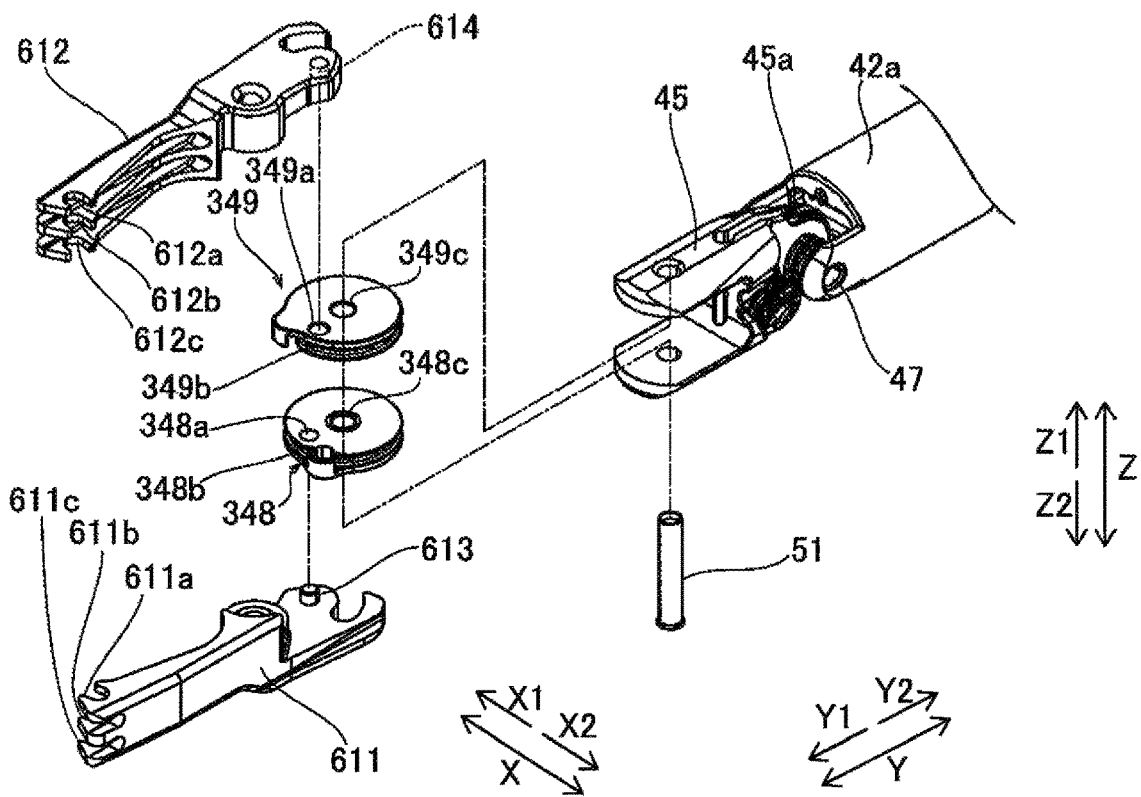
FIG. 14 is a diagram illustrating an exploded perspective view of the configuration around the end portion of the shaft of the surgical instrument according to a third embodiment.

As illustrated in FIGS. 13 and 14, the end effector 341 includes a first jaw 611 and a second jaw 612 that are opened and closed with respect to each other. The end effector 341 is configured to sandwich plural (two) clips C between the first jaw 611 and the second jaw 612. Accordingly, the first jaw 611 includes a plurality of (three) clip holder portions 611a, 611b and 611c. Also, the second jaw 612 includes a plurality of clip holder portions 612a, 612b and 612c, corresponding to the plurality of clip holder portions 611a, 611b and 611c of the first jaw 611. The clip holder portions 611a and 611b and the clip holder portions 612a and 612b hold a first clip C. The clip holder portions 611c and 611b and the clip holder portions 612c and 612b hold a second clip C. The clip holder portions 611b and 612b are configured to hold the first clip C and the second clip C.

Further, the end effector 341 is configured to clip the clipping target with the plural clips C at the same time by closing the first jaw 611 and the second jaw 612 with respect to each other. Further, the end effector 341 is configured to open and close by being rotated about the rotational axis A2 extending in the Z direction orthogonal to the X direction.

The surgical instrument 340 includes a pulley part 348 that rotates the first jaw 611 and a pulley part 349 that rotates the second jaw 612. The pulley part 348 is configured to support the first jaw 611 and thus rotate the first jaw 611. The pulley part 349 is configured to support the second jaw 612 and thus rotate the second jaw 612.

The pulley part 348 includes an engagement portion 348a, a pulley groove 348b, and a through hole 348c. The engagement portion 348a is configured to be engaged with an engagement portion 613 of the first jaw 611. The engagement portion 348a is configured as a through hole extending in the Z direction. The engagement portion 613 is configured as a convex part (a projection or a pin) extending in the Z1 direction. The pulley groove 348b is provided on which the driving element 46b (see FIG. 13) is wound. The pulley part 348 is driven to rotate by the driving element 46b passing in the pulley groove 348b, so that the first jaw 611, which is engaged with the engagement portion 348a, is rotated about the rotational axis A2 (see FIG. 13). The through hole 348c is provided to insert the rotational shaft 51 therein. The pulley part 348 is rotatably supported by the rotational shaft 51 supported on the support body 45. The pulley part 348 is provided to be rotatable about the rotation axis A3 (see FIG. 13) extending in the Z direction.

Similarly, the pulley part 349 includes an engagement portion 349a, a pulley groove 349b, and a through hole 349c. The engagement portion 349a is configured to be engaged with an engagement portion 614 of the second jaw 612. The engagement portion 349a is configured as a through hole extending in the Z direction. The engagement portion 614 is configured as a convex part (a projection or a pin) extending in the Z2 direction. The pulley groove 349b is provided on which the driving element 46b (see FIG. 13) is wound. The pulley part 349 is driven to rotate by the driving element 46b passing in the pulley groove 349b, so that the second jaw 612, which is engaged with the engagement portion 349a, is rotated about the rotational axis A2 (see FIG. 13). The through hole 349c is provided to insert the rotational shaft 51 therein. The pulley part 349 is rotatably supported by the rotational shaft 51 supported on the support body 45. The pulley part 349 is provided to be rotatable about the rotation axis A3 (see FIG. 13) extending in the Z direction.

Note that the other features of the configuration in the third embodiment are similar to the above first embodiment.

[Modifications]

It should be understood that one or more embodiments described above are illustrated by way of example in every respect and do not limit the disclosure. The scope of the invention is indicated by claims and includes equivalents to the claims and all alterations (modification) within the same.

For example, in first and second embodiments described above, the case has been described in which the number of the end effectors are two. However, the invention is not limited thereto. In the invention, the number of end effectors may be three or more.

Further, in first and second embodiments described above, the case has been described in which the plural end effectors include the clip applier, the scissors, or the needle holder. However, the invention is not limited to this. In the invention, the plural end effectors may include an end effector other than the clip applier, the scissors, and the needle holder.

Further, in first and second embodiments described above, the case has been described in which the extending direction of the rotational axis of each of the plural end effectors and the extending direction of the rotational axis of the support body are substantially orthogonal to each other. However, the invention is not limited to this. In the invention, the extending direction of the rotational axis of each of the plural end effectors and the extending direction of the rotational axis of the support body may be substantially parallel to each other.

Further, in first and second embodiments described above, the case has been described in which the common pulley parts are provided for the plural end effectors. However, the invention is not limited thereto. In the invention, a pulley part(s) may be provided for each of the plural end effectors. For example, a pulley part that rotates the first jaw of the first end effector, a pulley part that rotates the second jaw of the first end effector, a pulley part that rotates the first jaw of the second end effector, and a pulley part that rotates the second jaw of the end effector may be provided separately.

Further, in the first and second embodiments, the case where the plural end effectors are linked to each other to be moved in the reverse directions from each other and the case where the plural end effectors are independently opened and closed have been described. However, the invention is not limited thereto. In the invention, plural end effectors may be configured to be (synchronizingly) opened and closed together in the same direction at the same time.

Further, in a second embodiment described above, the case has been described in which the second jaw of the first end effector and the second jaw of the second end effector are rotated independently from each other, whereas the first jaw of the first end effector and the first jaw of the second end effector are rotated together. However, the invention is not limited thereto. In the invention, the first jaw of the first end effector and the first jaw of the second end effector may be rotated independently from each other, whereas the second jaw of the first end effector and the second jaw of the second end effector may be rotated together.

For example, in a third embodiment described above, the case has been described in which the one end effector is configured to be capable of holding two clips. However, the invention is not limited thereto. In the invention, the end effector may be configured to be capable of holding three or more clips.

In first to third embodiments described above, the case has been described in which the driving element is the wire. However, the invention is not limited to this. In the invention, the driving element may be a cable, a rod, or the like.

The invention claimed is:

1. A surgical instrument comprising:
    a housing that is to be attached to a driving unit of a robot arm and is provided with a plurality of driven members to be driven by a plurality of drive members of the driving unit of the robot arm;
    a shaft including one end portion and the other end portion, the one end portion of the shaft being connected to the housing;
    a plurality of end effectors;
    a support body that is rotatably supported by the other end portion of the shaft and rotatably supports the plurality of end effectors; and
    a plurality of driving elements that are respectively connected to the plurality of driven members to drive the plurality of end effectors and the support body to rotate, wherein
    the plurality of end effectors comprise a first end effector and a second end effector,
    each of the first end effector and the second end effector includes a first jaw and a second jaw that are opened and closed with respect to each other, and
    the plurality of end effectors include a first pulley part engaged with the first jaw of the first end effector and the second jaw of the second end effector and a second pulley part engaged with the second jaw of the first end effector and the first jaw of the second end effector.

2. The surgical instrument according to claim 1, wherein the plurality of end effectors comprise at least one of a clip applier and a pair of scissors.

3. The surgical instrument according to claim 1, wherein the plurality of end effectors comprise two clip appliers.

4. The surgical instrument according to claim 1, wherein the plurality of end effectors comprise a clip applier and a pair of scissors.

5. The surgical instrument according to claim 1, wherein an extending direction of a rotational axis of each of the plurality of end effectors and an extending direction of a rotational axis of the support body are substantially orthogonal to each other.

6. The surgical instrument according to claim 1, wherein a number of the plurality of end effectors is two.

7. The surgical instrument according to claim 1, wherein the plurality of end effectors are configured in such a manner that, when the first and second jaws of the first end effector are in an opening operation, the first and second jaws of the second end effector are in a closing operation, whereas when the first and second jaws of the first end effector are in a closing operation, the first and second jaws of the second end effector are in an opening operation.

8. The surgical instrument according to claim 1, wherein the first jaw of the first end effector and the first jaw of the second end effector are disposed on one side in a direction orthogonal to rotational axes of the first and second end effectors, whereas the second jaw of the first end effector and the second jaw of the second end effector are disposed on the other side in the direction orthogonal to the rotational axes of the first and second end effectors.

9. The surgical instrument according to claim 1, wherein the plurality of driving elements are wires, cables, or rods.

10. The surgical instrument according to claim 1, wherein the first pulley part and the second pulley part are configured to rotate about a common rotational axis.

11. The surgical instrument according to claim 10, wherein
    the first pulley part comprises three disc portions each having a substantially circular shape as seen along the rotational axis of the first and second pulley parts.

12. The surgical instrument according to claim 11, wherein
    the three disc portions of the first pulley part include: a first disc portion; a second disc portion; and a third disc portion provided between the first disc portion and the second disc portion in the direction of the rotational axis of the first and second pulley parts, and
    the third disc portion is formed, at an outer circumference thereof, with a pulley groove on which one of the driving elements is wound.

13. The surgical instrument according to claim 12, wherein
    the first disc portion, the second disc portion, and the third disc portion are connected to each other with a shaft portion extending in the direction of the rotational axis of the first and second pulley parts.

14. The surgical instrument according to claim 13, wherein
    the second pulley part includes a notch to be engaged with the shaft portion of the first pulley part.

15. A surgical instrument comprising:
    a housing that is to be attached to a driving unit of a robot arm and is provided with a plurality of driven members to be driven by a plurality of drive members of the driving unit of the robot arm;
    a shaft including one end portion and the other end portion, the one end portion of the shaft being connected to the housing;
    a plurality of end effectors;
    a support body that is rotatably supported by the other end portion of the shaft and rotatably supports the plurality of end effectors; and
    a plurality of driving elements that are respectively connected to the plurality of driven members to drive the plurality of end effectors and the support body to rotate, wherein
    the plurality of end effectors comprise a first end effector and a second end effector,
    each of the first end effector and the second end effector includes a first jaw and a second jaw that are opened and closed with respect to each other, and
    the plurality of end effectors comprise: a first pulley part that is provided with the first jaw of the first end effector and the first jaw of the second end effector to rotate the first jaw of the first end effector and the first jaw of the second end effector together; and a second pulley part that is provided with the second jaw of the first end effector to rotate the second jaw of the first end effector; and a third pulley part that is provided with the second jaw of the second end effector to rotate the second jaw of the second end effector.

16. The surgical instrument according to claim 15, wherein
the plurality of end effectors are configured to be opened and closed independently from each other.

17. The surgical instrument according to claim 15, wherein
the first jaw and the second jaw of the first end effector and the first jaw and the second jaw of the second end effector are configured to be rotatable about a rotational axis, and
the first pulley part is provided between the second pulley part and the third pulley part in an extending direction of the rotational axis.

18. The surgical instrument according to claim 15, wherein
the plurality of driven members comprise: a first driven member to drive the first pulley part to rotate; a second driven member to drive the second pulley part to rotate; a third driven member to drive the third pulley part to rotate; a fourth driven member to drive the support body to rotate; and a fifth driven member to drive the shaft to rotate.

19. A surgical instrument comprising:
a housing that is to be attached to a driving unit of a robot arm and is provided with a plurality of driven members to be driven by a plurality of drive members of the driving unit of the robot arm;
a shaft including one end portion and the other end portion, wherein the one end portion of the shaft is connected to the housing;
a plurality of end effectors at least one of which is a clip applier that is configured to hold plural clips;
a support body that is rotatably supported by the other end portion of the shaft and rotatably supports the plurality of end effectors; and
a plurality of driving elements that are respectively connected to the plurality of driven members to drive the plurality of end effectors and the support body to rotate, wherein
the plurality of end effectors comprise a first end effector and a second end effector,
each of the first end effector and the second end effector includes a first jaw and a second jaw that are opened and closed with respect to each other, and
the plurality of end effectors include a first pulley part engaged with the first jaw of the first end effector and the second jaw of the second end effector and a second pulley part engaged with the second jaw of the first end effector and the first jaw of the second end effector.

* * * * *